United States Patent
Ozaki

(10) Patent No.: US 9,880,132 B2
(45) Date of Patent: Jan. 30, 2018

(54) ENVIRONMENTAL MEASUREMENT APPARATUS AND ENVIRONMENTAL MEASUREMENT METHOD

(71) Applicant: FUJITSU LIMITED, Kawasaki-shi, Kanagawa (JP)

(72) Inventor: Mitsuo Ozaki, Isehara (JP)

(73) Assignee: FUJITSU LIMITED, Kawasaki (JP)

( * ) Notice: Subject to any disclaimer, the term of this patent is extended or adjusted under 35 U.S.C. 154(b) by 451 days.

(21) Appl. No.: 14/558,038

(22) Filed: Dec. 2, 2014

(65) Prior Publication Data

US 2015/0082865 A1 Mar. 26, 2015

Related U.S. Application Data

(63) Continuation of application No. PCT/JP2012/065023, filed on Jun. 12, 2012.

(51) Int. Cl.
  *G01N 29/036* (2006.01)
  *G01N 5/02* (2006.01)
  *G01N 15/06* (2006.01)

(52) U.S. Cl.
  CPC ........... *G01N 29/036* (2013.01); *G01N 5/02* (2013.01); *G01N 15/0606* (2013.01); *G01N 2291/021* (2013.01); *G01N 2291/0256* (2013.01); *G01N 2291/0426* (2013.01)

(58) Field of Classification Search
  CPC ......... G01N 29/036; G01N 2291/0256; G01N 2291/0426; G01N 2291/021; G01N 5/02; G01N 15/0606
  USPC .............................................. 73/24.01, 24.06
  See application file for complete search history.

(56) References Cited

U.S. PATENT DOCUMENTS

| 3,879,992 | A | * | 4/1975 | Bartera | G01B 7/066 310/312 |
| 3,895,912 | A | * | 7/1975 | Naumann | G01N 27/16 331/37 |
| 6,492,601 | B1 | * | 12/2002 | Cain | G01G 3/16 177/210 FP |
| 7,681,449 | B2 | * | 3/2010 | Wolf | G01N 17/04 73/24.01 |
| 8,034,295 | B2 | * | 10/2011 | Takasu | G01N 5/02 422/50 |

FOREIGN PATENT DOCUMENTS

| JP | 55-015080 | 2/1980 |
| JP | 6-011471 | 1/1994 |

(Continued)

OTHER PUBLICATIONS

International Search Report and Written Opinion of the International Searching Authority (Form PCT/ISA/210, Form PCT/ISA/237), mailed in connection with PCT/JP2012/065023 and dated Aug. 28, 2012 (7 pages).

(Continued)

*Primary Examiner* — Daniel S Larkin
(74) *Attorney, Agent, or Firm* — Fujitsu Patent Center

(57) ABSTRACT

An environmental measurement apparatus includes an operation unit which calculates a first change in a first oscillation frequency of a first QCM sensor and a second change in a second oscillation frequency of a second QCM sensor. The operation unit corrects the second change based on the first change in a first period and the second change in the first period.

5 Claims, 43 Drawing Sheets

(56) References Cited

FOREIGN PATENT DOCUMENTS

| | | |
|---|---|---|
| JP | 8-193937 | 7/1996 |
| JP | 11-066465 | 3/1999 |
| JP | 2001-099777 | 4/2001 |

OTHER PUBLICATIONS

JPOA—Office Action of Japanese Patent Application No. 2014-520842 dated Dec. 8, 2015, with partial English translation of the Office Action.
CNOA—Office Action of Chinese Patent Application No. 201280073869.8 dated Dec. 7, 2015, with English translation of the Office Action.
\*\* JP08-193937 cited in both Japanese and Chinese Office Actions was previously submitted in the IDS filed on Dec. 2, 2014. \*\*

\* cited by examiner

FIG. 14A  $t<t_s$
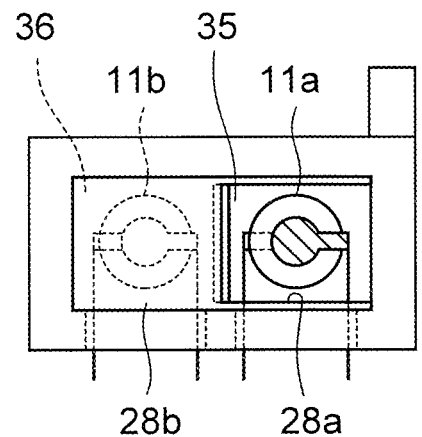
FIG. 14B  $t_s \leqq t \leqq t_c$
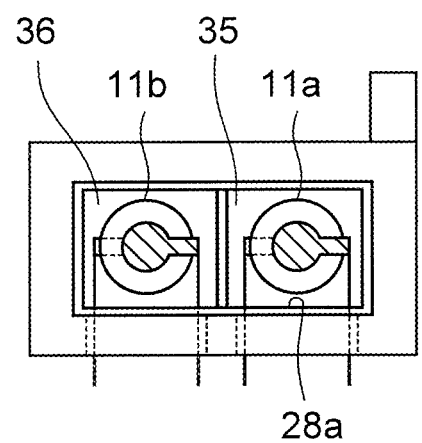
FIG. 14C  $t_c<t$
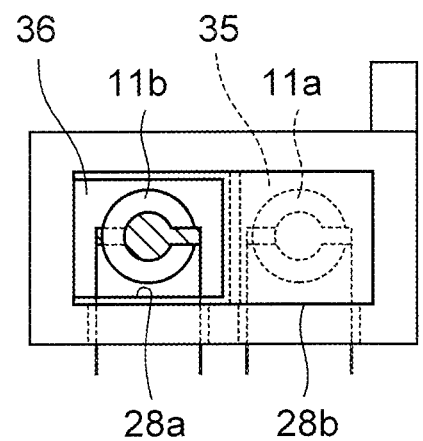

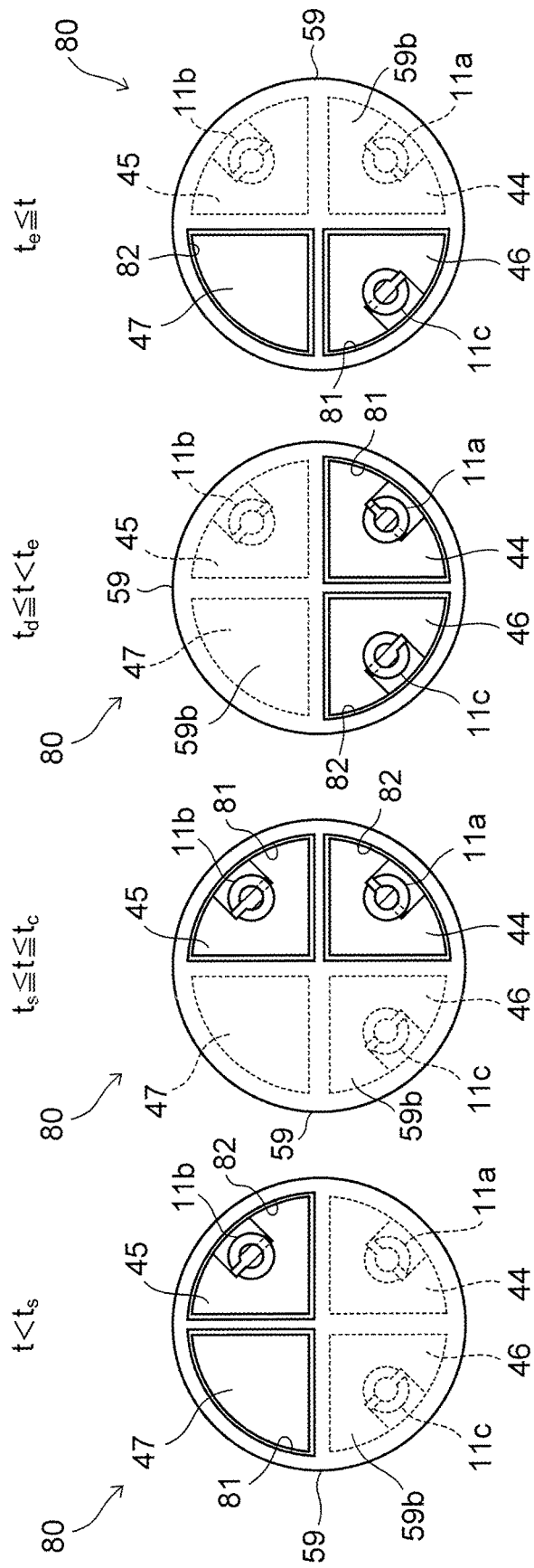

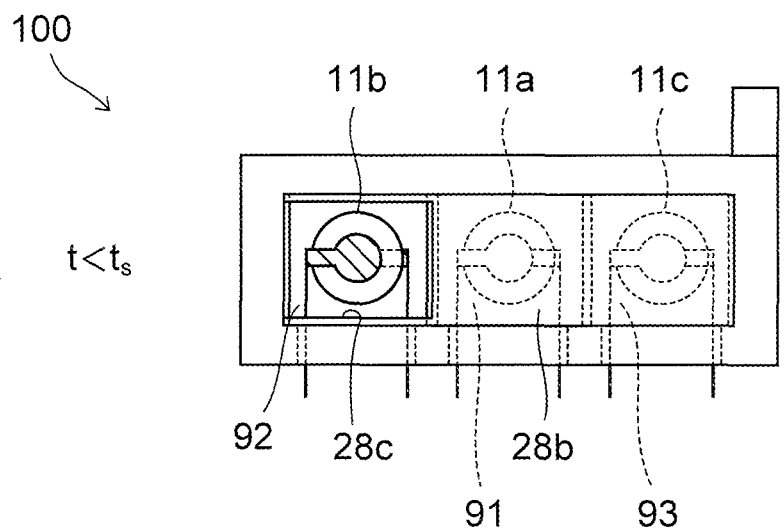
FIG. 41A  $t<t_s$
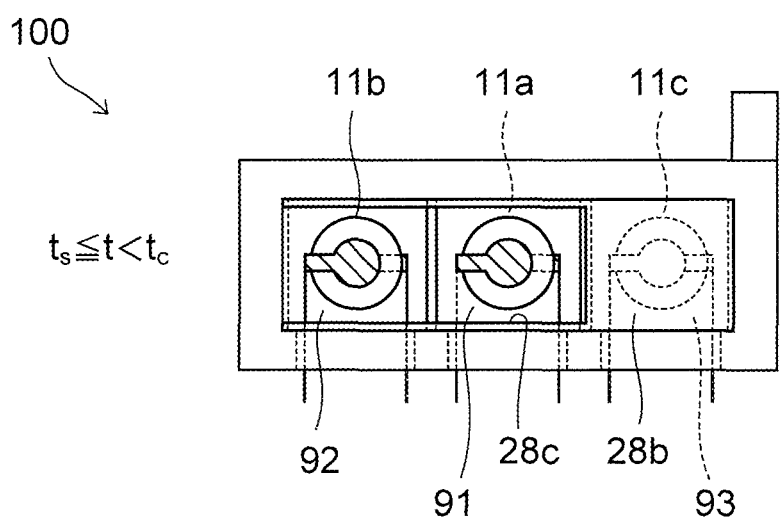
FIG. 41B  $t_s \leqq t < t_c$
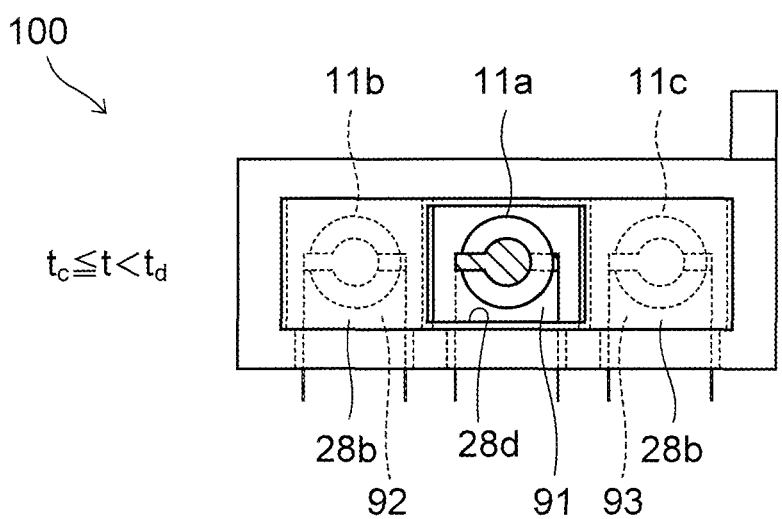
FIG. 41C  $t_c \leqq t < t_d$

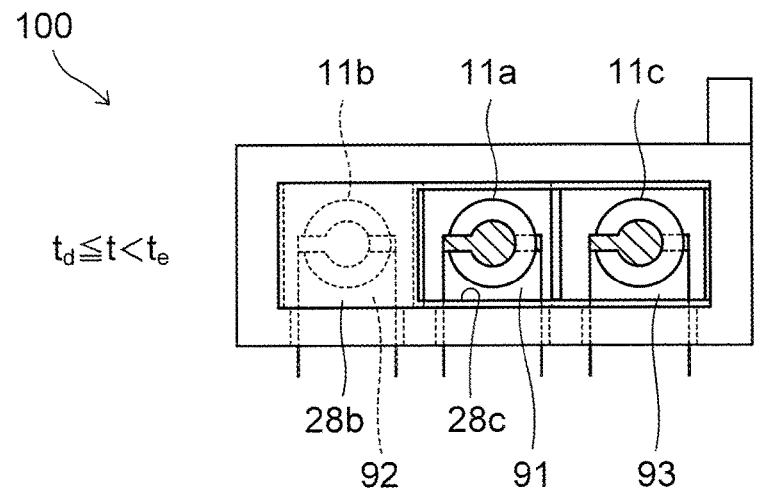
FIG. 41D  $t_d \leqq t < t_e$
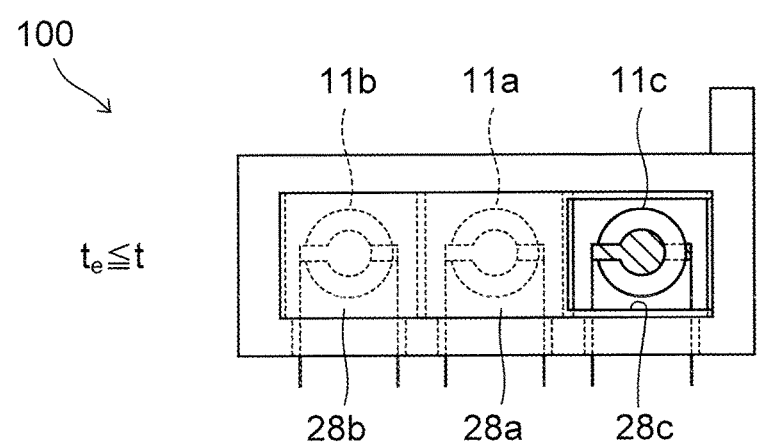
FIG. 41E  $t_e \leqq t$

US 9,880,132 B2

ENVIRONMENTAL MEASUREMENT APPARATUS AND ENVIRONMENTAL MEASUREMENT METHOD

CROSS-REFERENCE TO RELATED APPLICATION(S)

This application is a continuation application of International Application PCT/JP2012/65023 filed on Jun. 12, 2012 and designated the U.S., the entire contents of which are incorporated herein by reference.

FIELD

The embodiments discussed herein are related to an environmental measurement apparatus and an environmental measurement method.

BACKGROUND

In some cases, the atmosphere contains corrosive gases that corrode electronic devices. The emission sources of the corrosive gases include a chemical plant such as a paper mill and a rubber factory, a waste treatment plant, a sewage treatment plant, a volcano, commodities containing chemicals, and the like.

One of the corrosive gases emitted from such emission sources is hydrogen sulfide gas. The hydrogen sulfide gas can corrode wires in an electronic device and break the electronic device. Particularly, in the case where an information society uses electronic devices to support the foundation of the system in social infrastructure, breakdown of the electronic devices may paralyze social activities.

In order to prevent breakdown of electronic devices due to the corrosive gas, it is useful to monitor the corrosive gas contained in an environment where the electronic devices are installed and to know in advance a possibility of the electronic devices breaking down due to corrosion caused by the corrosive gas.

A QCM (Quartz Crystal Microbalance) sensor is known as a sensor to monitor the corrosive gas. The QCM sensor is a mass sensor capable of measuring a minute change in mass by using a property that, when the mass of electrodes on a crystal oscillator is changed by corrosion, the crystal oscillator reduces its oscillation frequency according to the amount of the corrosion.

In the QCM sensor, a change in the oscillation frequency grows as the amount of corrosion is increased over time, and the QCM sensor comes to the end of its life. For this reason, in the case of monitoring the corrosive gas over a long time period, it is preferable that a QCM sensor whose life is close to the end be replaced with a new QCM sensor to prevent a blank period in monitoring.

However, since QCM sensors have individual differences, the replaced QCM sensor cannot necessarily maintain the measurement accuracy for the amount of corrosion caused by the corrosive gas.

SUMMARY

According to one aspect of the following disclosure, there is provided an environmental measurement apparatus including an operation unit which calculates a first change in a first oscillation frequency of a first QCM sensor and a second change in a second oscillation frequency of a second QCM sensor, wherein the operation unit corrects the second change based on the first change in a first period and the second change in the first period.

According to another aspect of the following disclosure, there is provided an environmental measurement method, the method including calculating a first change in a first oscillation frequency of a first QCM sensor; calculating a second change in a second oscillation frequency of a second QCM sensor; and correcting the second change based on the first change in a first period and the second change in the first period.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIGS. 14A to 14C are plan views for explaining operations of the sensor unit used in the second embodiment;

FIGS. 37A to 37D are plan views for explaining operations of the sensor unit included in the environmental measurement apparatus according to the sixth embodiment;

FIGS. 41A to 41E are plan views for explaining operations of the sensor unit included in the environmental measurement apparatus according to the seventh embodiment.

DESCRIPTION OF EMBODIMENTS

Prior to description of embodiments, the result of examination conducted by the inventor of the present application is described. In this examination, the individual differences between QCM sensors are examined as follows.

Figure 1:
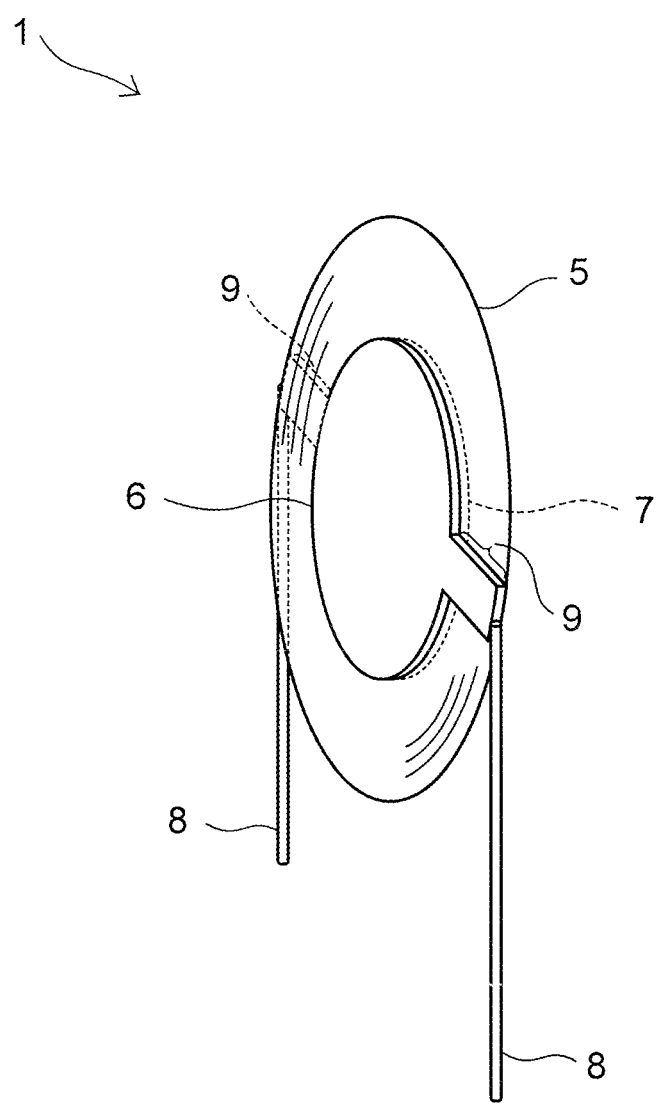
FIG. 1 is a perspective view of a QCM sensor used in an examination.

FIG. 1 is a perspective view of a QCM sensor 1 used in the examination.

The QCM sensor 1 includes a disk-shaped crystal oscillator 5, a first electrode 6 formed on one main surface of the crystal oscillator 5, and a second electrode 7 formed on the other main surface of the crystal oscillator 5.

The size and cut of the crystal oscillator 5 are not particularly limited. In this examination, an AT-cut crystal oscillator 5 of 8 mm in diameter is used.

Also, the materials of the first and second electrodes 6 and 7 are selected according to a corrosive gas to be detected. For example, in the case of detecting hydrogen sulfide, silver can be used as the material of the first and second electrodes 6 and 7. Alternatively, in the case of detecting chlorine, copper can be used as the material of the first and second electrodes 6 and 7.

Moreover, conductive wires 8 made of gold or the like are electrically connected to the first and second electrodes 6 and 7 through lead wires 9, respectively. The crystal oscillator 5 is supported by the conductive wires 8.

In actual use, the crystal oscillator 5 is oscillated by applying a predetermined voltage between the first and second electrodes 6 and 7 through the conductive wires 8. The crystal oscillator 5 is oscillated at a oscillation frequency called a fundamental frequency F at the start of its use. However, as the mass of the first and second electrodes 6 and 7 increases due to corrosion, the oscillation frequency f is gradually decreased.

Here, a change $\Delta f_m$ (=F−f) in the frequency f when the total mass of the first and second electrodes 6 and 7 is increased by $M_f$ compared with the start of the use is expressed by the following Sauerbrey equation (1).

$$\Delta f_m = -\frac{2F^2}{\sqrt{\rho_q \mu_q}} \frac{M_f}{S} \tag{1}$$

Here, F denotes fundamental oscillation frequency, $\rho_q$ denotes density of quartz, $\rho_q$ is shear stress of quartz, and S is total surface area of the first and second electrodes 6 and 7.

In the early period of measuring an amount of corrosion caused by the corrosive gas using the QCM sensor 1, corrosion of the first and second electrodes 6 and 7 progresses according to the concentration of the corrosive gas in the environment. Therefore, in this period, a time change occurring in the increase $M_f$ of the mass can be read with good sensitivity as $\Delta f_m$ by the Sauerbrey equation (1).

However, when the corrosion reaches large portions of the first and second electrodes 6 and 7, the corrosion of the electrodes slows down and eventually goes into saturation. Therefore, $\Delta f_m$ can no longer be read from the mass increase $M_f$. Moreover, even before the corrosion stops, a load on the oscillation of the crystal oscillator 5 is increased too much by the increase of mass of the first and second electrodes 6 and 7 due to the corrosion. As a result, the oscillation frequency may exceed a stable oscillation range and become unstable. In such a case, the corrosive gas cannot be monitored any more with the QCM sensor 1, and the QCM sensor 1 comes to the end of its life.

When the QCM sensor comes to the end of its life in this manner, the old QCM sensor is replaced with a new QCM sensor in order to continue long-term monitoring of the amount of corrosion caused by the corrosive gas. In this event, when the old and new QCM sensors have different specifications, the proportionality constant $(-2F^2/(\rho_q \mu_q)^{1/2})$ on the right-hand side of Equation (1) changes from the one before the replacement. This makes it impossible to grasp variations in the amount of corrosion caused by the corrosive gas before and after the replacement. As a result, the accuracy of measurement of the amount of corrosion caused by the corrosive gas is reduced.

Therefore, when replacing the old QCM sensor with a new one, it is preferable to replace the QCM sensor with one having the same specifications as those of the old one. Here, the specifications of the QCM sensor include the size and pane of the crystal oscillator 5, the size and material of each of the first and second electrodes 6 and 7, and the like, for example.

However, despite the attempt to use the QCM sensors with the same specifications, variations in material and processing at the time of manufacture actually cause the proportionality constant on the right-hand side of Equation (1) to take values that vary from one QCM sensor to another. Moreover, the way the electrodes are corroded also varies from one QCM sensor to another. This leads to individual difference in corrosion characteristics of the QCM sensors.

Figure 2A:
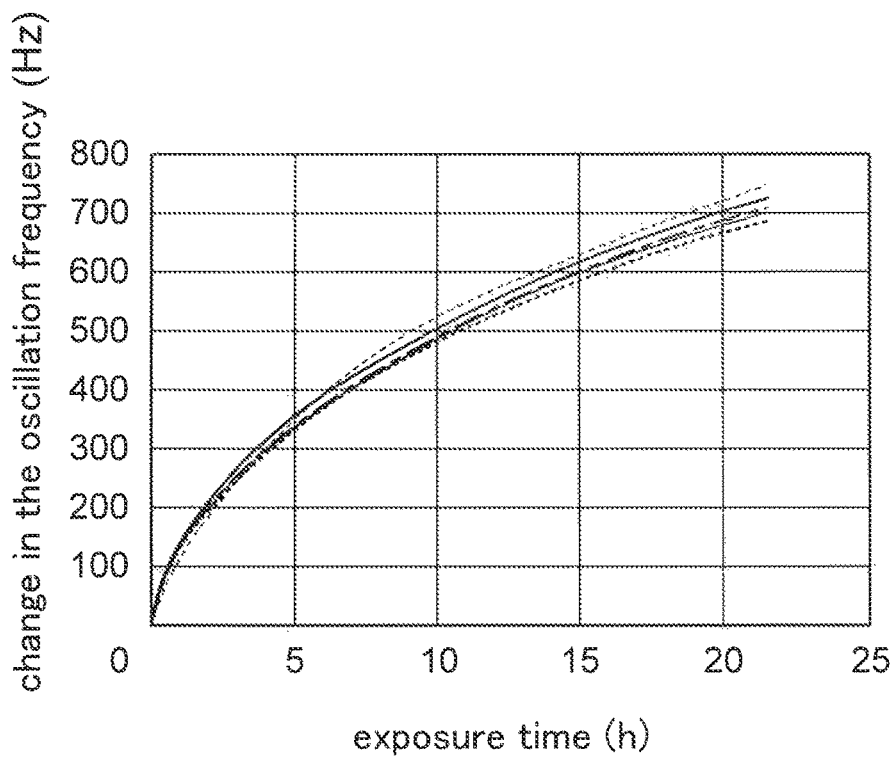
FIGS. 2A and 2B are graphs obtained by examining individual variations of the QCM sensors.
Figure 2B:
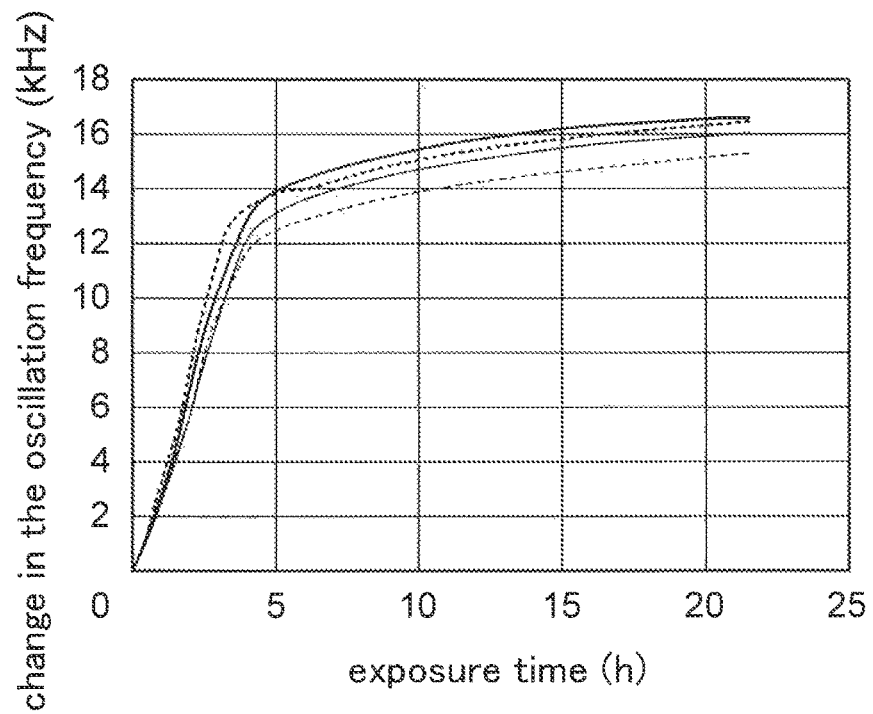

FIGS. 2A and 2B are graphs obtained by examining such individual differences.

FIG. 2A illustrates the result obtained by using silver as the material of the first and second electrodes 6 and 7 and exposing the QCM sensor 1 to an atmosphere containing hydrogen sulfide. Note that the temperature of the atmosphere is 25° C. and the relative humidity thereof is 50%. Also, the concentration of the hydrogen sulfide in the atmosphere is 0.25 ppm.

In FIG. 2A, the horizontal axis represents exposure time of the QCM sensor 1 to the atmosphere described above, while the vertical axis represents the change $\Delta f_m$ in the oscillation frequency.

Although FIG. 2A illustrates a plurality of graphs, these graphs are obtained by using QCM sensors having the same specifications within the same lot.

The graphs do not completely overlap with each other, and the change in oscillation frequency varies by up to about 10% between the graphs. In the case of QCM sensors from different lots, graphs are expected to vary more than those illustrated in FIG. 2A.

Thus, it was confirmed that QCM sensors show individual differences even if they have the same specification.

FIG. 2B is a graph obtained by using a metal layer having a two-layer structure as each of the first and second electrodes 6 and 7 and conducting the same examination as that illustrated in FIG. 2A. Note that a gold layer that serves to electrically connect each of the electrodes 6 and 7 to the wire 8 is formed as a lowermost layer of the metal layer having the two-layer structure, and a copper layer is formed as metal to be corroded in an uppermost layer.

Note that when the first and second electrodes 6 and 7 are formed to have a multi-layer structure in this manner, a metal layer may be formed between layers to increase adhesion between the layers. Moreover, a metal layer may be formed between the first electrode 6 and the crystal oscillator 5 to increase their adhesion strength. Furthermore, a metal layer may be formed between the second electrode 7 and the crystal oscillator 5 to increase their adhesion strength.

In this case, again, it was found out that the QCM sensors show individual difference as in the case of FIG. 2A.

Such individual difference causes a difference in tendency of measured values between the old QCM sensor that has reached the end of its life and the new QCM sensor after replacement. This makes it difficult to monitor with high accuracy the amount of corrosion caused by the corrosive gas in the atmosphere over a long time.

In order to predict the individual differences of the QCM sensors, it is also conceivable to create graphs as illustrated in FIGS. 2A and 2B by actually corroding the QCM sensors in the early stage of the measurement. However, this method does not necessarily allow the corrosion to progress as expected, and ends up shortening the life of the QCM sensor by the amount of corrosion.

In the following, the embodiments are described.

First Embodiment

In this embodiment, a corrosive gas is monitored over a long time by replacing the old QCM sensor with the new QCM sensor. Moreover, the measurement accuracy of the amount of corrosion caused by the corrosive gas is maintained by taking into consideration the individual difference of the old and new QCM sensors during replacement.

Figure 3:
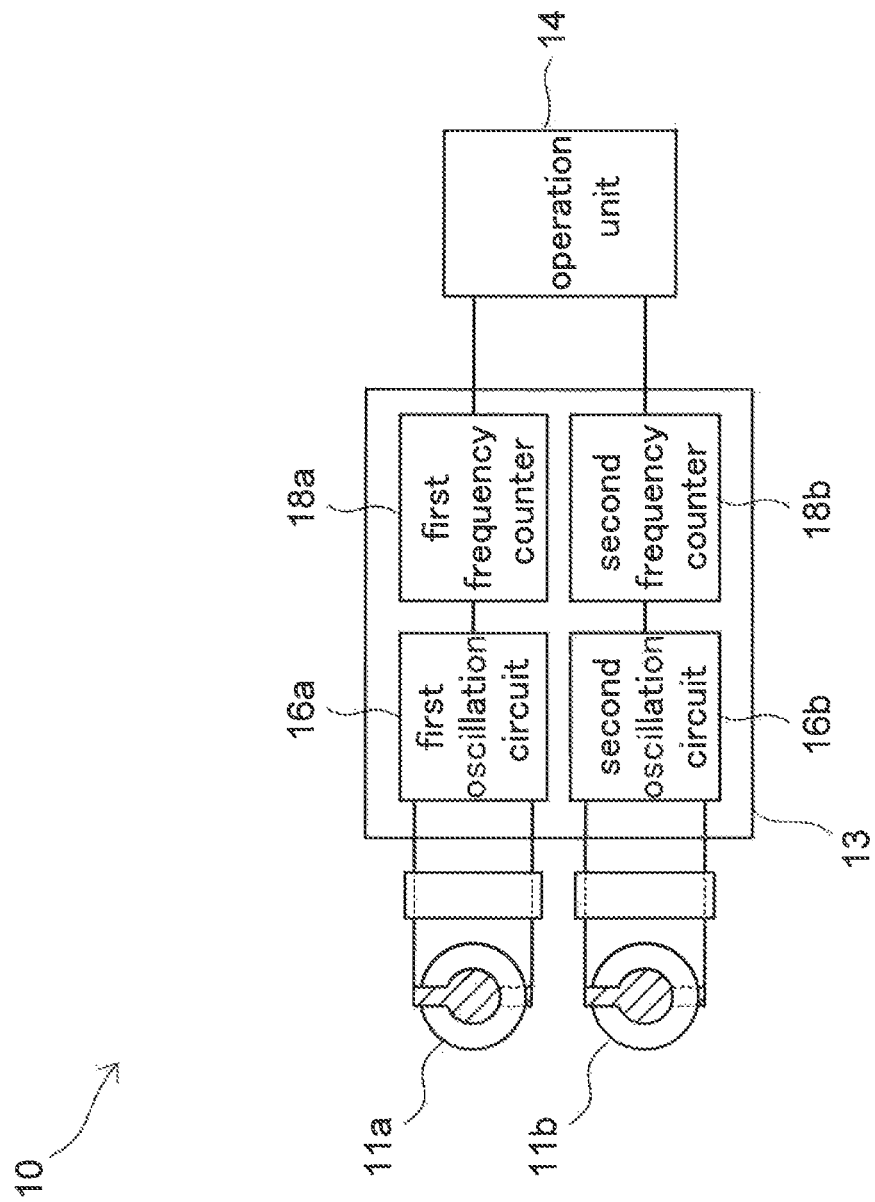
FIG. 3 is a configuration diagram of an environmental measurement apparatus according to a first embodiment.

FIG. 3 is a configuration diagram of an environmental measurement apparatus according to this embodiment.

The environmental measurement apparatus 10 includes a drive unit 13 and an operation unit 14.

The drive unit 13 is connected to an old first QCM sensor 11a before replacement and a new second QCM sensor 11b after replacement.

Note that the first and second QCM sensors 11a and 11b have the same structure as that illustrated in FIG. 1 and have the same specifications. In this embodiment, a crystal oscillator 5 in each of the first and second QCM sensors 11a and 11b is 8 mm in diameter, and a silver film having a thickness of 0.1 μm is formed as each of electrodes 6 and 7. Also, the fundamental oscillation frequency of the first and second QCM sensors 11a and 11b is 25 MHz, for example.

Furthermore, aging treatment may be performed to corrode the electrodes 6 and 7 in the first and second QCM sensors 11a and 11b to some extent in advance. The aging treatment enables measurement within a more stable corrosion characteristic range while avoiding a sudden change in corrosion characteristics in the early stage of the measurement as illustrated in FIGS. 2A and 2B. This is also the case for the embodiments to be described later.

The drive unit 13 includes first and second oscillation circuits 16a and 16b and first and second frequency counters 18a and 18b.

The first and second oscillation circuits 16a and 16b are circuits to oscillate the first and second QCM sensors 11a and 11b, respectively, at their fundamental oscillation frequency.

Figure 4:
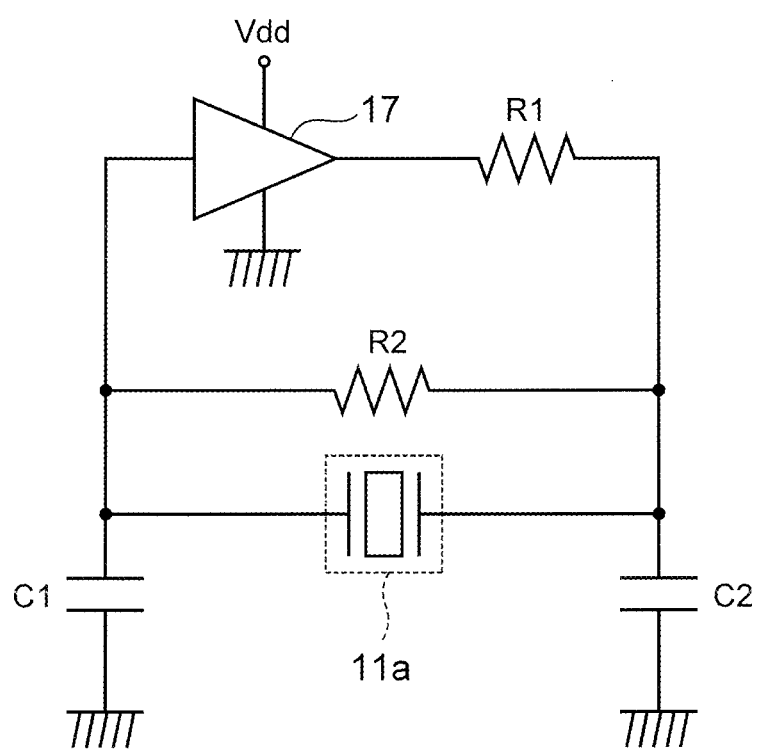
FIG. 4 is a circuit diagram of an oscillation circuit included in the environmental measurement apparatus according to the first embodiment.

FIG. 4 is a circuit diagram of the first oscillation circuit 16a. Note that a circuit diagram of the second oscillation circuit 16b is the same as that illustrated in FIG. 4, and thus description thereof is omitted here.

As illustrated in FIG. 4, the first oscillation circuit 16a includes an inverter 17, first and second resistors R1 and R2, and first and second capacitors C1 and C2. By properly setting values thereof, the first QCM sensor 11a can be stably oscillated at a predetermined oscillation frequency.

In such a circuit, the inverter 17 forms a parallel oscillation circuit with the first QCM sensor 11a, and the first QCM sensor 11a can be oscillated by appropriately setting capacitance values of the first and second capacitors C1 and C2.

Note that the magnitude of crystal current flowing through the first QCM sensor 11a is adjusted by the first resistor R1. A power-supply voltage Vdd is applied to the inverter 17, and the second resistor R2 functions as a feedback resistor of the inverter 17.

FIG. 3 is referred to again.

The first frequency counter 18a is connected to the first oscillation circuit 16a to measure a first oscillation frequency $f_{1m}$ of the first QCM sensor 11a. Likewise, the second frequency counter 18b is connected to the second oscillation circuit 16b to measure a second oscillation frequency $f_{2m}$ of the second QCM sensor 11b.

The operation unit 14 is a computer such as a personal computer, and acquires the first oscillation frequency $f_{1m}$ and the second oscillation frequency $f_{2m}$ from the drive unit 13.

Figure 5:
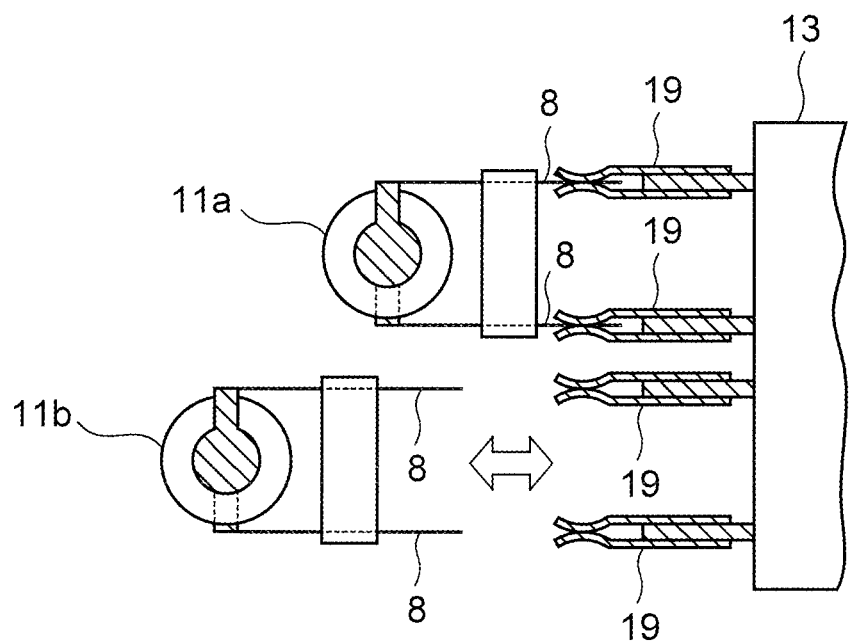
FIG. 5 is an enlarged view around connectors in a drive unit included in the environmental measurement apparatus according to the first embodiment.

FIG. 5 is an enlarged view around connectors in the drive unit 13.

As illustrated in FIG. 5, the drive unit 13 is provided with four connectors 19, to and from which the conductive wires 8 in the first and second QCM sensors 11a and 11b can be attached and detached.

In this embodiment, a user firstly inserts the first QCM sensor 11a into the connectors 19 and monitors the amount of corrosion caused by the corrosive gas in the atmosphere with the first QCM sensor 11a. Then, as the life of the first QCM sensor 11a approaches its end, the user attaches the new second QCM sensor 11b to the connectors 19.

Figure 6:
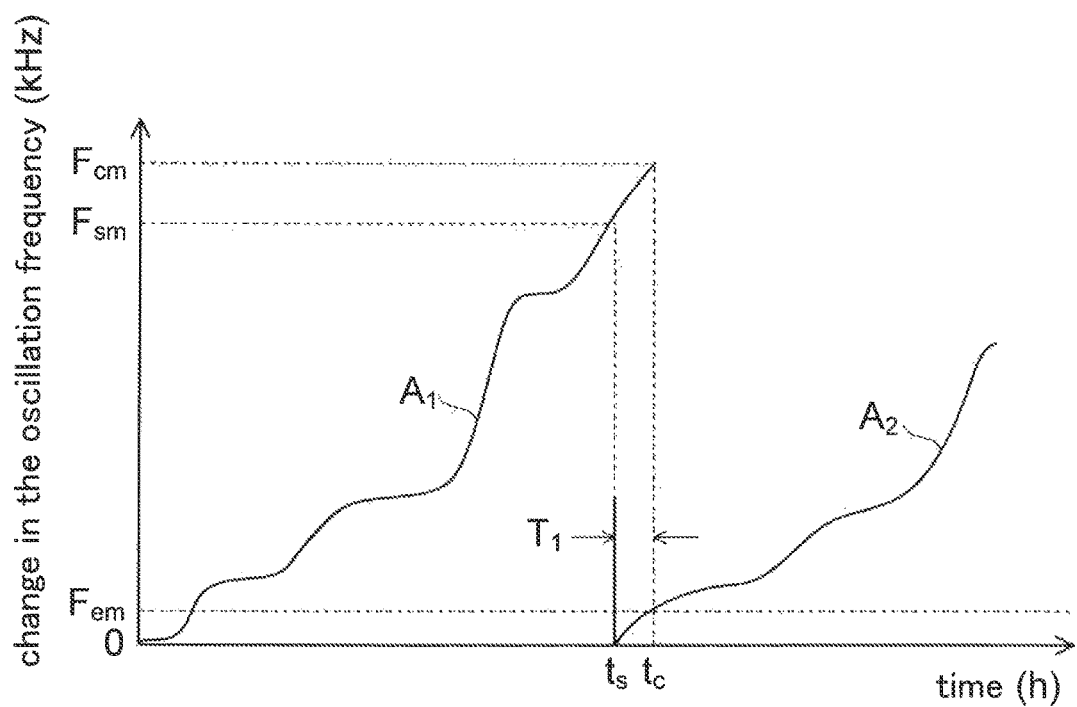
FIG. 6 is a graph illustrating an example of a result of measurement using QCM sensors included in the environmental measurement apparatus according to the first embodiment.

FIG. 6 is a graph illustrating an example of a result of measurement using the first and second QCM sensors 11a and 11b.

Note that the horizontal axis of FIG. 6 represents time that has elapsed since the start of measurement with the first QCM sensor 11a. Also, the vertical axis of FIG. 6 represents a first change $\Delta f_{1m}$ in the first oscillation frequency $f_{1m}$ of the first QCM sensor 11a and a second change $\Delta f_{2m}$ in the second oscillation frequency $f_{2m}$ of the second QCM sensor 11b.

Let $F_1$ and $F_2$ be the fundamental frequencies of the first and second QCM sensors 11a and 11b respectively. Then, the changes $\Delta f_{1m}$ and $\Delta f_{2m}$ are defined as $\Delta f_{1m}=F_1-f_{1m}$ and $\Delta f_{2m}=F_2-f_{2m}$ respectively.

Also, in FIG. 6, the first change $\Delta f_{1m}$ is represented by a first graph $A_1$ and the second change $\Delta f_{2m}$ is represented by a second graph $A_2$.

In this embodiment, as illustrated in FIG. 6, a first period $T_1$ is provided, during which the measurement is conducted with both of the first and second QCM sensors 11a and 11b.

A first time $t_s$, which is the beginning of the first period $T_1$, is the time when the first change $\Delta f_{1m}$ in the oscillation frequency of the first QCM sensor 11a reaches a predetermined first specified value $F_{sm}$.

A second time $t_c$, which is the end of the first period $T_1$, is the time when the first change $\Delta f_{1m}$ reaches a predetermined second specified value $F_{cm}$.

As to the specified values, the second specified value $F_{cm}$ is the first change $\Delta f_{1m}$ at which the first QCM sensor 11a is determined to have reached the end of its life. Meanwhile, the first specified value $F_{sm}$ is the first change $\Delta f_{1m}$ at which the first QCM sensor 11a is determined to be close to the end of its life.

A method for setting the first specified value $F_{sm}$ is not particularly limited. For example, another QCM sensor having the same specifications as those of the first QCM sensor 11a is actually corroded, and a change in oscillation frequency when the QCM sensor comes to the end of its life is measured. Then, a value smaller by about 1 to 5% than the change can be set as the first specified value $F_{sm}$. Moreover, in this embodiment, correction is performed using the changes $\Delta f_{1m}$ and $\Delta f_{2m}$ in the first period $T_1$, as described later. Therefore, the longer the first period $T_1$, the more data needed for the correction can be collected.

Note that, taking the individual differences in the specification of the QCM sensors into consideration, it is preferable that the specified value $F_{cm}$ is set in anticipation of a certain amount of margin. By increasing the margin in this manner, more reliable and accurate correction can be performed. However, in order to prevent reduction in a period during which measurement can be performed before replacement of the QCM sensor, i.e., the substantial life, it is preferable that the specified value $F_{cm}$ is set to an appropriate value in consideration of the purpose of measurement and the like.

During the first period $T_1$, the corrosive gas in the same atmosphere is monitored using the first and second QCM sensors 11a and 11b having the same specifications. Therefore, corrosion rates obtained from results of measurement using the first and second QCM sensors 11a and 11b, i.e., rates of changes in frequency, are expected to be the same.

However, variations in the measurement results due to the individual difference as described above cause a difference in the slope of the graph (corrosion rate) during the first period $T_1$ between the first and second QCM sensors 11a and 11b as illustrated in FIG. 6.

To deal with this problem, in this embodiment, the slope of the second graph $A_2$ is matched with the slope of the first graph $A_1$ by correcting the second change $\Delta f_{2m}$ of the second QCM sensor 11b as follows.

Figure 7:
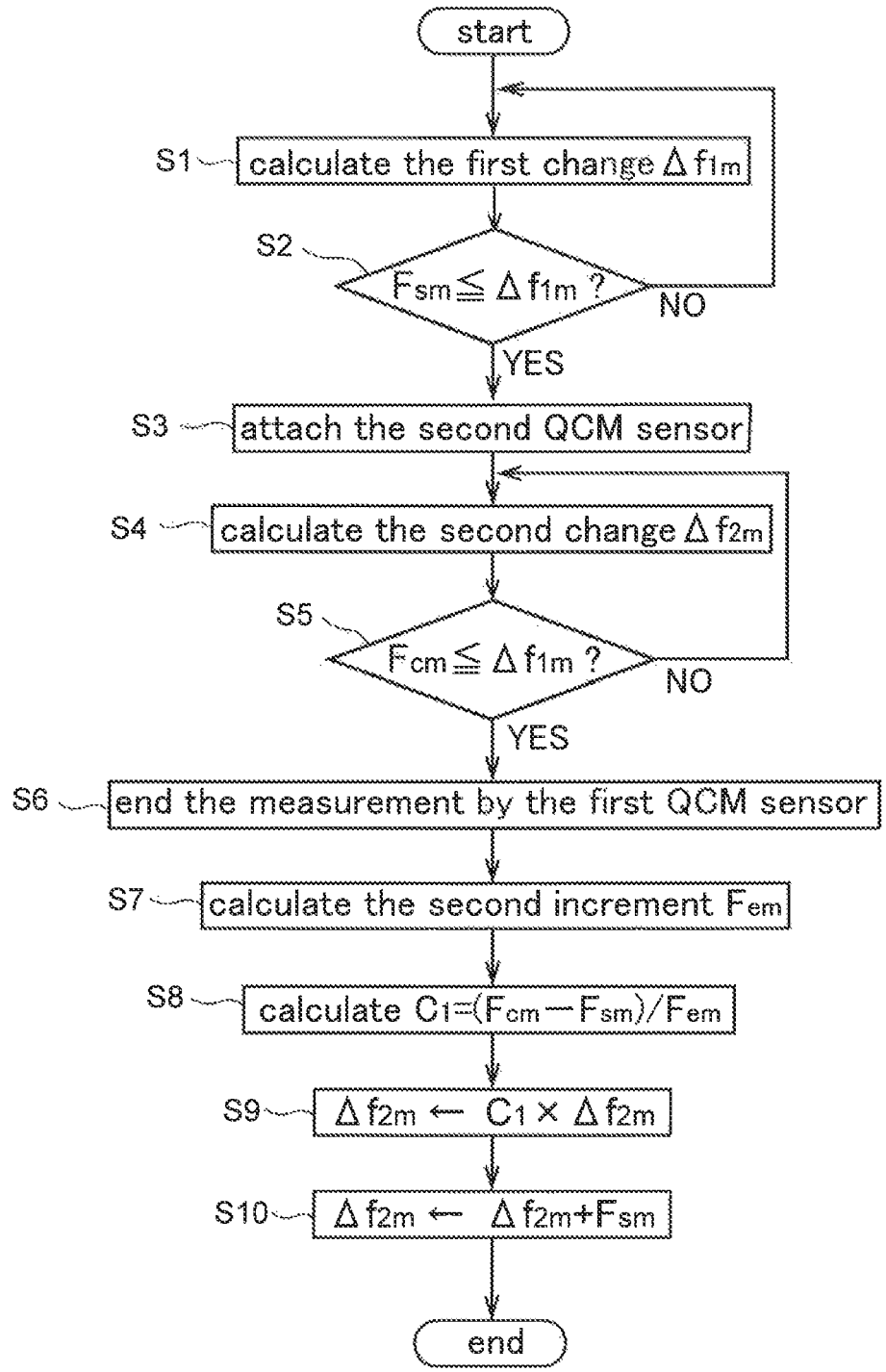
FIG. 7 is a flowchart for explaining an environmental measurement method according to the first embodiment.

FIG. 7 is a flowchart for explaining an environmental measurement method according to this embodiment.

In the first Step S1, the operation unit 14 acquires the first oscillation frequency $f_{1m}$ of the first QCM sensor 11a at a time t, and calculates the first change $\Delta f_{1m}$ in the oscillation frequency $f_{1m}$ at the time t. The first change $\Delta f_{1m}$ is a difference $(F_1-f_{1m})$ between the fundamental frequency $F_1$ which is the oscillation frequency of the first QCM sensor 11a at time 0 and the first oscillation frequency $f_{1m}$ at the time t.

Next, in Step S2, the operation unit 14 determines whether or not the first change $\Delta f_{1m}$ is equal to or more than the first specified value $F_{sm}$.

Here, when it is determined that the first change $\Delta f_{1m}$ is not equal to or more than the first specified value $F_{sm}$ (NO), the first QCM sensor 11a is considered to be not close to the end of its life yet. Thus, the processing returns to Step S1 to continue the measurement using the first QCM sensor 11a.

On the other hand, when it is determined in Step S2 that the first change $\Delta f_{1m}$ is equal to or more than the first specified value $F_{sm}$ (YES), the time t is within the aforementioned first period $T_1$. Thus, it is considered that the life of the first QCM sensor 11a is coming close to the end.

Therefore, in this case, the processing moves to Step S3, where the user attaches the new second QCM sensor 11b to the drive unit 13 to prepare for measurement using the second QCM sensor 11b.

Next, in Step S4, the operation unit 14 starts acquiring the second oscillation frequency $f_{2m}$ of the second QCM sensor 11b. Considering the labor for attaching the second QCM sensor 11b or the like, the start time is slightly behind the first time $t_s$ about a few seconds to a few minutes. However, the second oscillation frequency $f_{2m}$ is substantially started to be acquired at the first time $t_s$.

Then, the operation unit 14 starts calculating the second change $\Delta f_{2m}$ in the second oscillation frequency $f_{2m}$ at the time t. The second change $\Delta f_{2m}$ is a difference $(F_2-f_{2m})$ between the fundamental frequency $F_2$ which is the oscillation frequency of the second QCM sensor 11b at the first time $t_s$ and the second oscillation frequency $f_{2m}$ at the time t.

Next, in Step S5, the operation unit 14 determines whether or not the first change $\Delta f_{1m}$ is equal to or more than the second specified value $F_{cm}$.

Here, when it is determined that the first change $\Delta f_{1m}$ is not equal to or more than the second specified value $F_{cm}$ (NO), it is considered that the life of the first QCM sensor 11a is approaching the end but does not yet reach the end. Thus, the processing returns to Step S4.

On the other hand, when it is determined in Step S5 that the first change $\Delta f_{1m}$ is equal to or more than the second specified value $F_{cm}$ (YES), it is considered that the first QCM sensor 11a come to the end of its life.

Thus, in this case, the processing moves to Step S6 to end the acquisition of the first oscillation frequency $f_{1m}$ with the first QCM sensor 11a. The end time is the second time $t_c$ when the first change $\Delta f_{1m}$ becomes equal to the second specified value $F_{cm}$.

Then, in Step S7, the operation unit 14 calculates the second change $\Delta f_{2m}$ at the second time $t_c$. Hereinafter, the second change $\Delta f_{2m}$ thus calculated is described as $F_{em}$ in this embodiment. $F_{em}$ corresponds to an increment of the second change $\Delta f_{2m}$ within the first period T1, and is an example of a second increment.

Thereafter, in Step S8, the operation unit 14 calculates a first correction coefficient $C_1$ to correct the second change $\Delta f_{2m}$ at and after the first time $t_s$.

Figure 8:
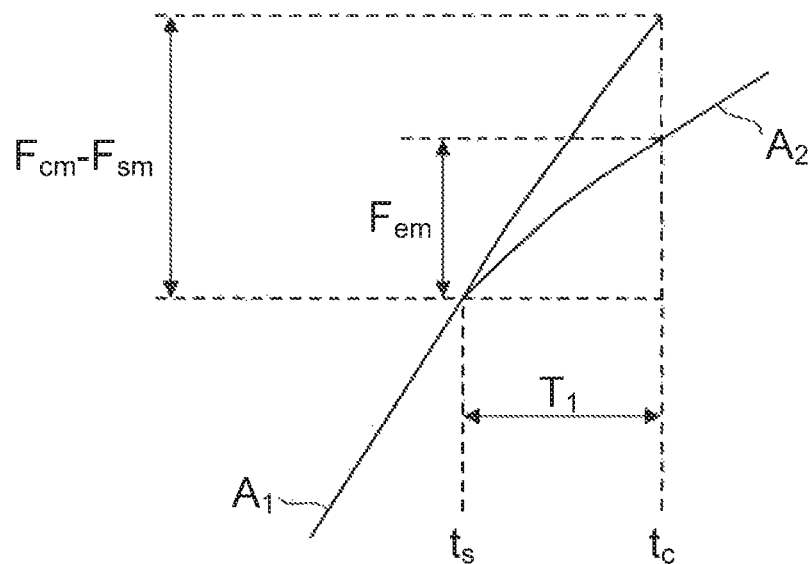
FIG. 8 is a diagram for explaining a method for calculating a first correction coefficient in the first embodiment.

FIG. 8 is a diagram for explaining a method for calculating the first correction coefficient $C_1$. In FIG. 8, the graph $A_2$ illustrated in FIG. 6 is translated in the vertical axis direction to match the starting point of the graph $A_2$ with the graph $A_1$ at the first time $t_s$.

Due to a difference in slope between the graphs $A_1$ and $A_2$, the graphs $A_1$ and $A_2$ cannot be connected by simply translating the graph in the vertical axis direction.

In this step, in order to resolve such a difference in slope, the operation unit 14 calculates the first correction coefficient $C_1$ by which the second change $\Delta f_{2m}$ is to be multiplied as follows.

First, a first increment $F_{em}-F_{sm}$ of the first change $\Delta f_{1m}$ within the first period $T_1$ is calculated.

Next, a first ratio $(F_{em}-F_{sm})/F_{em}$ of the first increment $F_{em}-F_{sm}$ to the second increment $F_{em}$ is calculated, and the first ratio is set as the first correction coefficient $C_1$. The first correction coefficient $C_1$ thus calculated is equal to a ratio between the slopes of the graphs $A_1$ and $A_2$ in FIG. 6 during the period $T_1$.

Then, in Step S9, the operation unit 14 corrects the second change $\Delta f_{2m}$ by multiplying the second change $\Delta f_{2m}$ at and after the first time $t_s$ by the first correction coefficient $C_1$.

As described above, the first correction coefficient $C_1$ is equal to the ratio between the slopes of the graphs $A_1$ and $A_2$. Therefore, by multiplying the second change $\Delta f_{2m}$ by the first correction coefficient $C_1$ in this step, the graph $A_2$ can be corrected to match the slope thereof with the slope of the graph $A_1$.

However, only the slopes of the graphs $A_1$ and $A_2$ are matched in this step, and heights of the graphs are not matched.

Therefore, in Step S10, the second change $\Delta f_{2m}$ is corrected again by further adding the first specified value $F_{sm}$, which is the first change $\Delta f_{1m}$ at the first time $t_s$, to the correction value $(C_1 \times \Delta f_{2m})$ calculated in Step S9.

Figure 9:
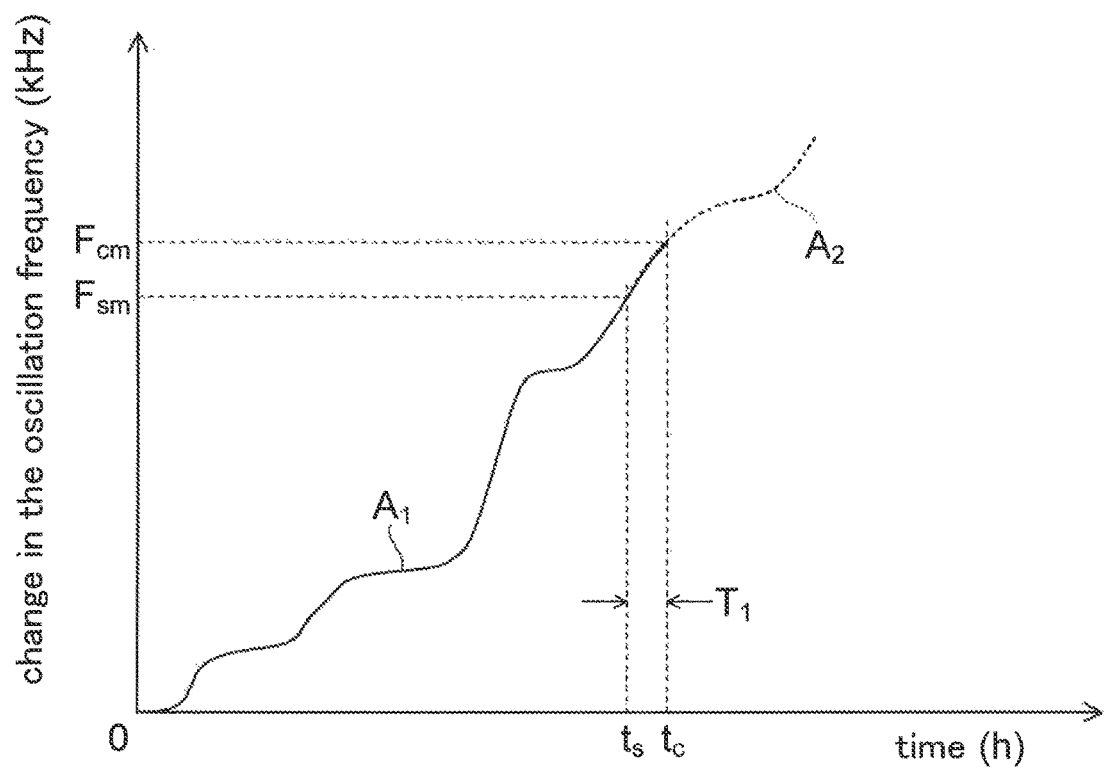
FIG. 9 is a diagram illustrating a second graph after correction in the first embodiment.

FIG. 9 is a diagram illustrating the second graph $A_2$ after the correction.

As illustrated in FIG. 9, due to the correction made in Step S9, the slope of the graph $A_2$ in the first period $T_1$ coincides with the slope of the graph $A_1$. Moreover, the heights of the graphs $A_1$ and $A_2$ are matched by the correction made in Step S10.

Thus, the basic steps of the environmental measurement method according to this embodiment are completed.

According to this embodiment described above, as illustrated in FIG. 9, the corrosive gas in the atmosphere can be monitored over a long time by using the first and second QCM sensors 11a and 11b.

Moreover, by correcting the second change $\Delta f_{2m}$ of the second QCM sensor 11b, it can be prevented that the measurement result becomes inaccurate due to the individual difference between the first and second QCM sensors 11a and 11b. Thus, the corrosive gas can be accurately monitored over the long time.

Second Embodiment

In the first embodiment, the QCM sensor, whose life is about to end, is replaced with a new one by user's own hand. In this embodiment, the QCM sensor is automatically replaced as follows.

Figure 10:
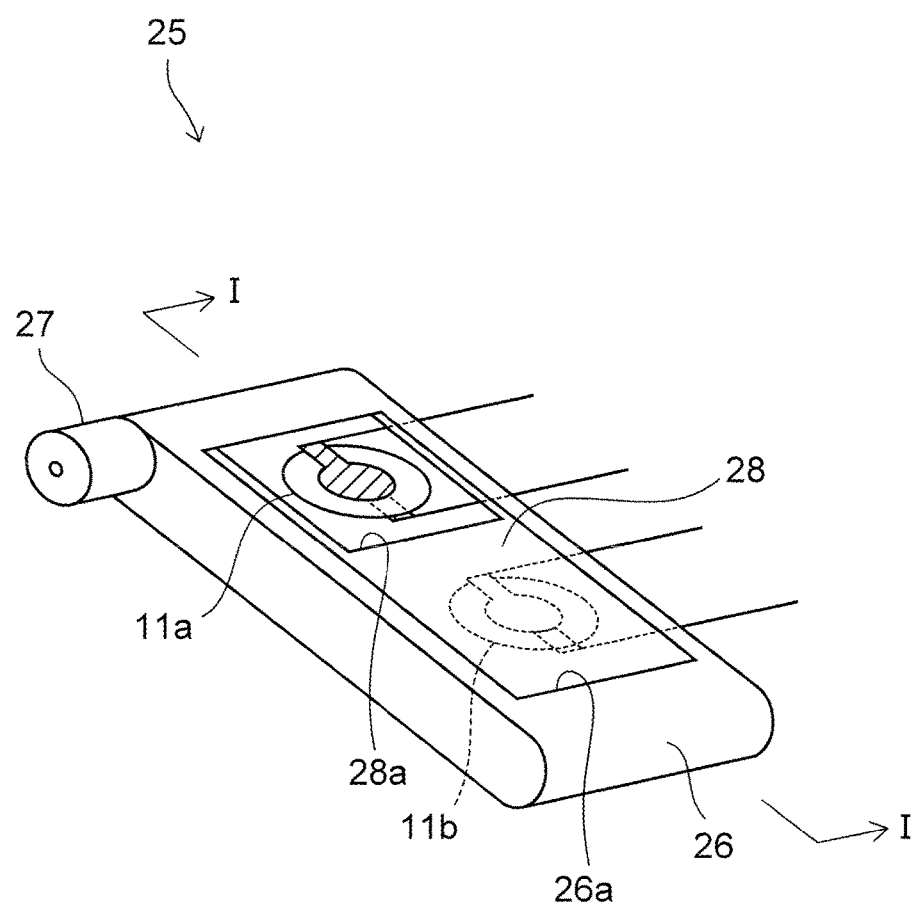
FIG. 10 is a perspective view of a sensor unit used in a second embodiment.

FIG. 10 is a perspective view of a sensor unit used in this embodiment.

The sensor unit 25 includes a housing 26 and a film-like shutter 28.

An opening 26a is provided in the housing 26, and a first QCM sensor 11a and a second QCM sensor 11b are housed in the opening 26a. Although the material of the housing 26 is not particularly limited, resin or metal is used as the material thereof in this embodiment.

The shutter 28 can be moved in a longitudinal direction thereof by a motor 27, and has a window 28a which overlaps with the opening 26a.

Figure 11:
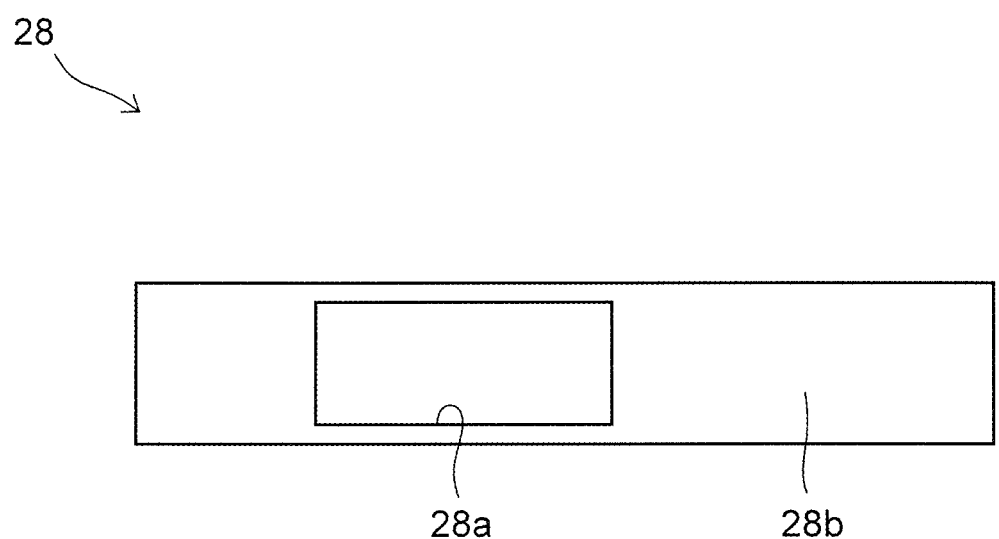
FIG. 11 is a development diagram of a shutter included in the sensor unit used in the second embodiment.

FIG. 11 is a development diagram of the shutter 28.

The shutter 28 is formed by processing a flexible film such as a resin film, and the window 28a has a rectangular shape in a planar view. Moreover, a portion of the shutter 28, in which the window 28a is not formed, is used as a shield portion 28b to cover the opening 26a.

Figure 12:
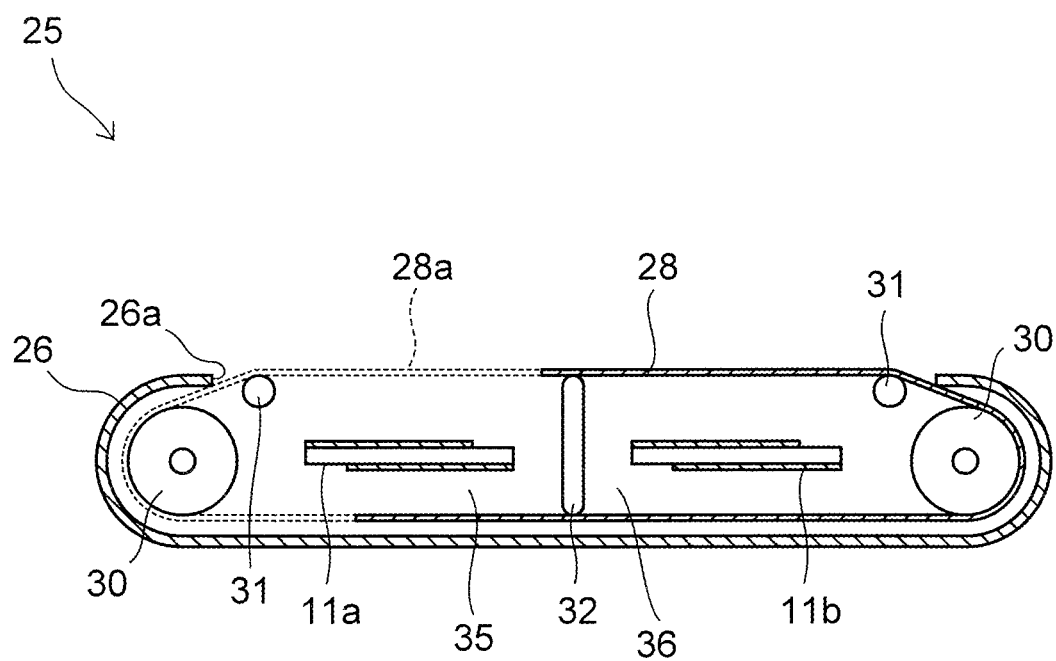
FIG. 12 is a cross-sectional view taken along the line I-I in FIG. 10.

FIG. 12 is a cross-sectional view taken along the line I-I in FIG. 10.

As illustrated in FIG. 12, the shutter 28 is wound around two rollers 30 in the housing 26, and the tension of the shutter 28 is adjusted by auxiliary rollers 31.

Also, a partition plate 32 is provided in the housing 26. The partition plate 32 is a resin plate or metal plate, and separates a space in the housing 26 into a first room 35 and a second room 36.

Figure 13:
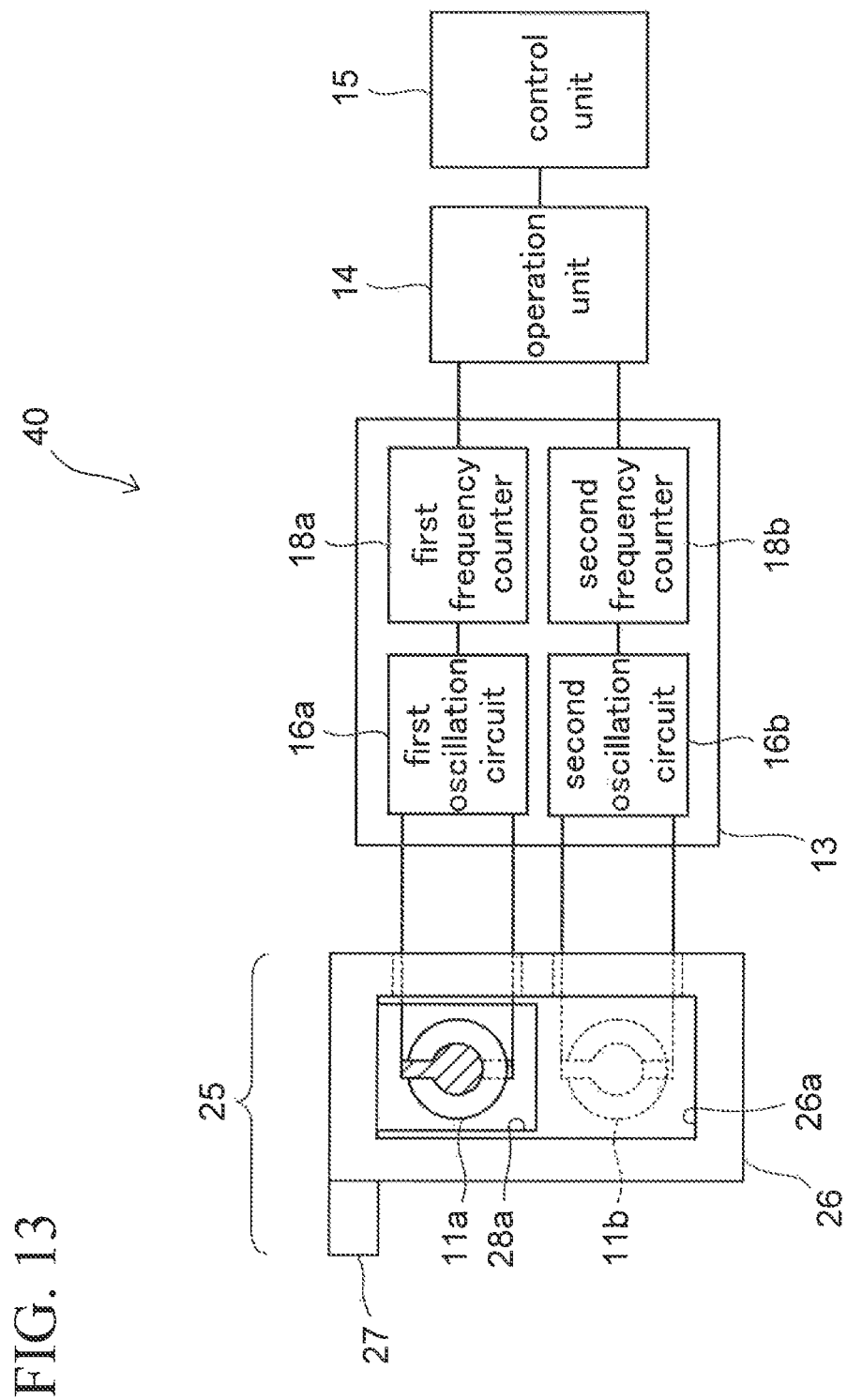
FIG. 13 is a configuration diagram of an environmental measurement apparatus according to the second embodiment.

FIG. 13 is a configuration diagram of an environmental measurement apparatus 40 including the sensor unit 25. Note that, in FIG. 13, the same components as those described in the first embodiment are denoted by the same reference numerals as those in the first embodiment, and description thereof is omitted below.

As illustrated in FIG. 13, a first QCM sensor 11a and a second QCM sensor 11b in the sensor unit 25 are connected to a drive unit 13.

Also, a control unit 15 to control a rotation amount of the motor 27 in the sensor unit 25 is provided at the subsequent stage of an operation unit 14. In this embodiment, a computer such as a personal computer is used as the control unit 15.

Next, operations of the sensor unit 25 are described.

FIGS. 14A to 14C are plan views for explaining the operations of the sensor unit 25.

FIG. 14A illustrates a state where a time t is before a first time $t_s$. At this time, as described in the first embodiment, the first QCM sensor 11a is not close to the end of its life yet, and the amount of corrosion caused by a corrosive gas is measured by using only the first QCM sensor 11a.

Therefore, at this time, the first QCM sensor 11a is exposed to the atmosphere containing the corrosive gas by communicating the window 28a of the shutter 28 with the first room 35. Moreover, in order to prevent corrosion of electrodes 6 and 7 in a new second QCM sensor 11b, the second room 36 is covered with the shield portion 28b of the shutter 28.

FIG. 14B illustrates a state where the time t is between the first time $t_s$ and a second time $t_e$.

Since this time is within the first period $T_1$ described in the first embodiment, correction is performed using both of the first and second QCM sensors 11a and 11b. Thus, at this time, the first and second QCM sensors 11a and 11b are both exposed to the atmosphere containing the corrosive gas by communicating the window 28a with each of the first and second rooms 35 and 36.

FIG. 14C illustrates a state where the time t is after the second time $t_e$. At this time, as described in the first embodiment, the amount of corrosion caused by the corrosive gas is measured by using the new second QCM sensor 11b.

Therefore, in this case, the second QCM sensor 11b is exposed to the atmosphere containing the corrosive gas by communicating the window 28a with the second room 36. Note that, since the measurement using the first QCM sensor 11a is finished, the first room 35 housing the first QCM sensor 11a is covered with the shield portion 28b.

According to this embodiment described above, as illustrated in FIGS. 14A to 14C, the control unit 15 automatically selects one of the first and second QCM sensors 11a and 11b that is to be exposed to the atmosphere, in accordance with the time t. Thus, burden of a user can be lessened Furthermore, the new second QCM sensor 11b is housed in the sensor unit 25 in advance, thereby reducing the labor for attaching the second QCM sensor 11b to the drive unit 13.

Moreover, the second QCM sensor 11b is housed in the second room 36 and not exposed to the corrosive gas outside until the life of the first QCM sensor 11a comes closer to the end. Thus, corrosion of the electrodes 6 and 7 in the new second QCM sensor 11b can also be prevented.

Note that, since the measurement using the first QCM sensor 11a is finished in the state of FIG. 14C, there is no influence on the measurement even when the state is changed to the state of FIG. 14B instead of the state of FIG. 14C. However, in terms of suppressing contamination of the connectors 19 and the inside of the first room 35 housing the first QCM sensor 11a, it is preferable that the first QCM sensor 11a is shielded with the shield portion 28b as illustrated in FIG. 14C.

Third Embodiment

In the second embodiment, the long shutter 28 is used as illustrated in FIG. 11. Meanwhile, in this embodiment, a circular shutter is used as described below.

Figure 15:
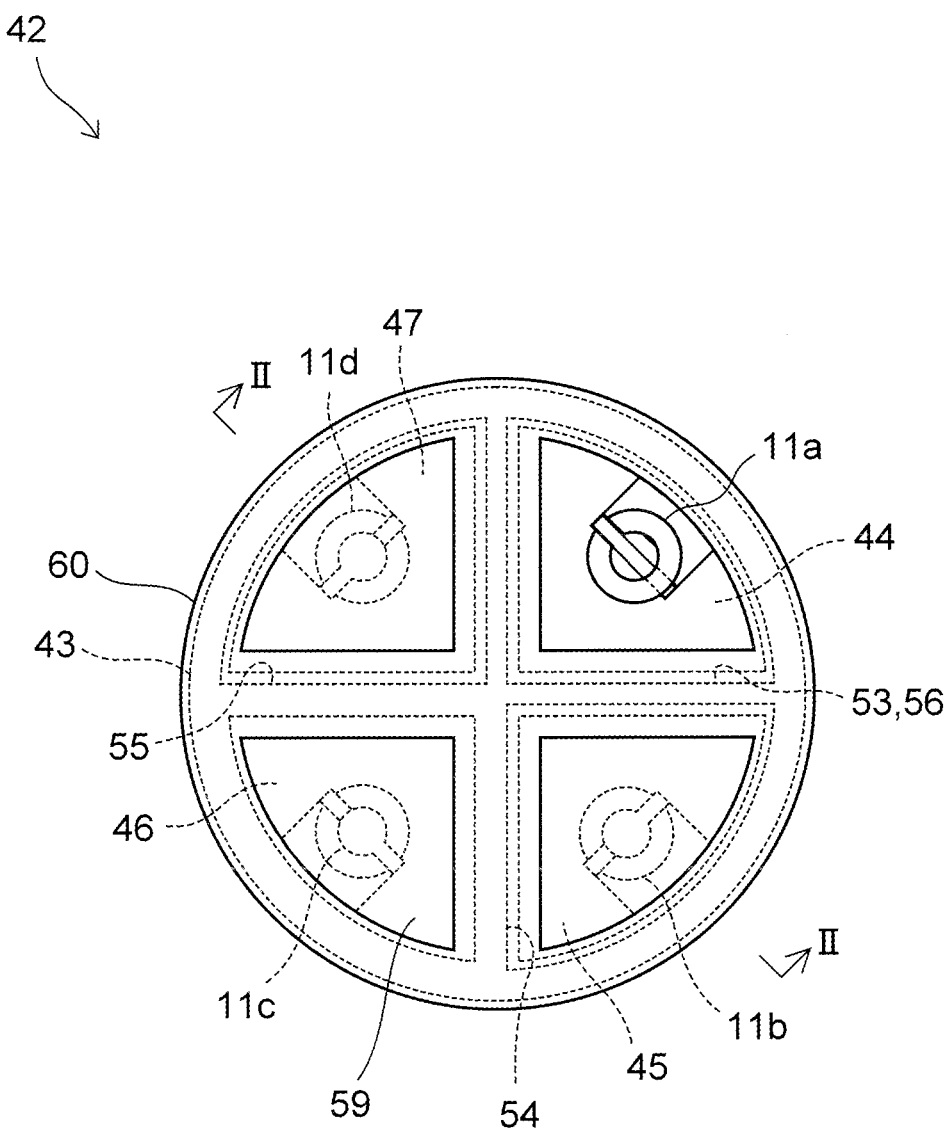
FIG. 15 is a plan view of a sensor unit used in a third embodiment.

FIG. 15 is a plan view of a sensor unit used in this embodiment.

The sensor unit 42 includes a housing 43 having a cylindrical shape in a planar view, a circular shutter 59, and a cap 60 placed on the shutter 59.

The shutter 59 is formed by overlaying two rotating plates capable of rotating independently of each other as described later, and edge of the shutter 59 overlaps with the housing 43.

The housing 43 is formed by shaping resin or metal, and includes first to fourth rooms 44 to 47 therein. In the first to fourth rooms 44 to 47, first to fourth QCM sensors 11a to 11d are housed, respectively. Note that the QCM sensors 11a to 11d have the same structure as that illustrated in FIG. 1, and thus description thereof is omitted.

Also, the cap 60 has a cross-shaped bar provided in a circular ring.

Figure 16A:
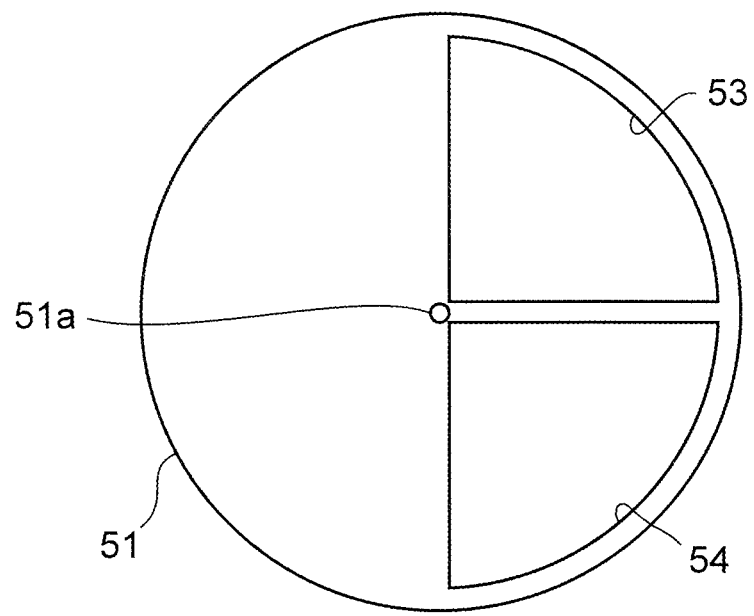
FIG. 16A is a plan view of a first rotating plate used in the third embodiment.
Figure 16B:
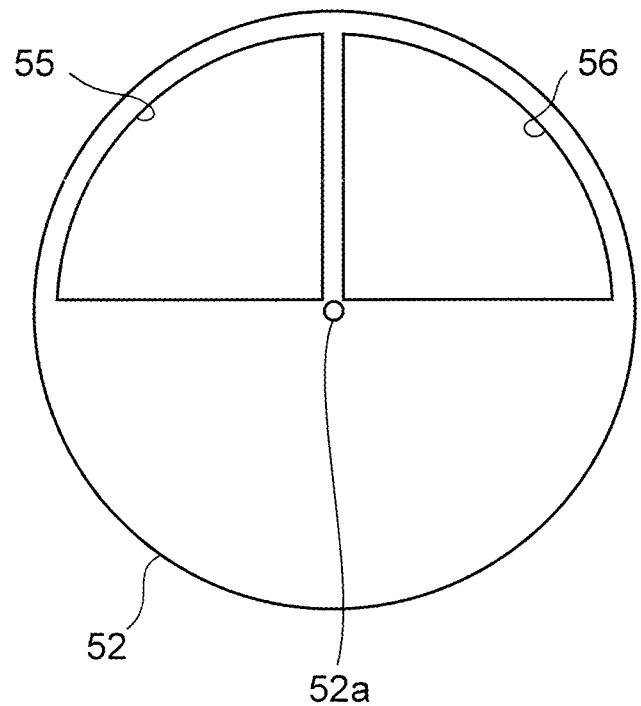
FIG. 16B is a plan view of a second rotating plate 52 used in the third embodiment.

FIG. 16A is a plan view of a first rotating plate 51 used as the shutter 59. FIG. 16B is a plan view of a second rotating plate 52 used together with the first rotating plate 51.

As illustrated in FIG. 16A, the first rotating plate 51 has a circular shape in a planar view. Also, the first rotating plate 51 can rotate about a first shaft 51a, and includes a first opening 53 and a second opening 54. The shape of the openings is not particularly limited. In this embodiment, the first and second openings 53 and 54 are formed to have a fan shape extending from the first shaft 51a toward the rim of the first rotating plate 51.

As illustrated in FIG. 16B, the second rotating plate 52 also has the same circular shape as that of the first rotating plate 51.

The second rotating plate 52 can rotate about a second rotating shaft 52a and includes third and fourth openings 55 and 56 having the same shape as that of the first and second openings 53 and 54 described above.

Note that both of the first and second rotating plates 51 and 52 are metal plates or resin plates.

Figure 17A:
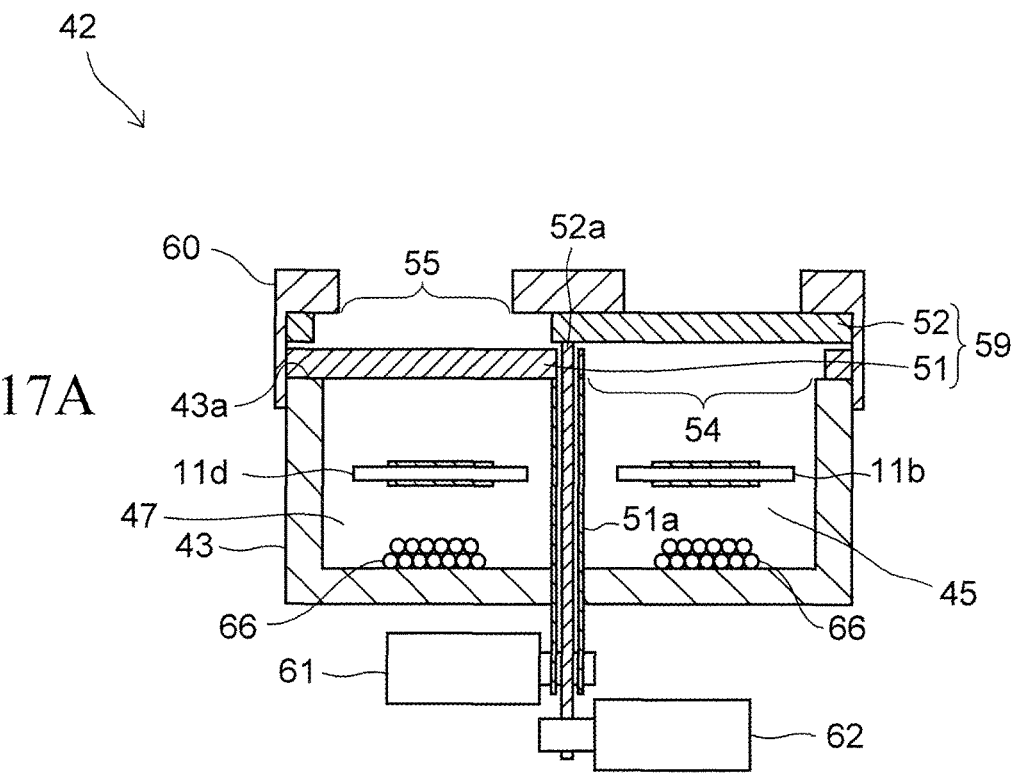
FIG. 17A is a cross-sectional view taken along the line II-II in FIG. 15.

FIG. 17A is a cross-sectional view taken along the line II-II in FIG. 15.

As illustrated in FIG. 17A, the first and second rotating plates 51 and 52 are sequentially overlaid on an opening edge 43a of the housing 43.

The cap 60 has an inner side surface fixed to an outer peripheral side surface of the housing 43. The cap 60 also slides on an upper surface of the second rotating plate 52, thereby suppressing rattling of the first and second rotating plates 51 and 52.

Moreover, a desiccant 66 such as silica gel is provided in each of the rooms 44 to 47. The electrodes 6 and 7 in the first to fourth QCM sensors 11a to 11d are corroded by a corrosive gas. The larger the amount of moisture in the atmosphere is, the faster the corrosion rate is. Therefore, by using the desiccant 66 to maintain the rooms 44 to 47 in a low-relative humidity state, the life of the first to fourth QCM sensors 11a to 11d can be prevented from being shortened by the progress of corrosion of the electrodes 6 and 7 in the sensors before monitoring the corrosive gas.

Furthermore, the desiccant 66 has the property to adsorb not only moisture but also the corrosive gas and the like. Thus, such an effect can also be expected that the desiccant 66 cleans the atmosphere in each of the rooms 44 to 47 storing the first to fourth QCM sensors 11a to 11d.

Figure 17B:
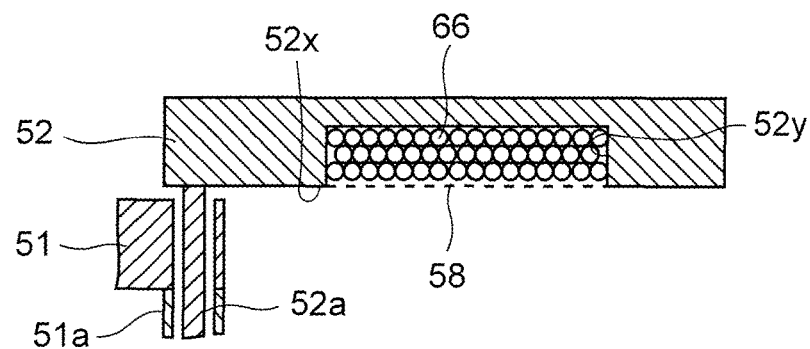
FIG. 17B is an enlarged cross-sectional view when a desiccant is housed in the second rotating plate.

The position to house the desiccant 66 is not limited to the above. FIG. 17B is an enlarged cross-sectional view when the desiccant 66 is housed in the second rotating plate 52.

Note that, in FIG. 17B, the same components as those described with reference to FIG. 17A are denoted by the same reference numerals as those in FIG. 17A, and description thereof is omitted below.

In the example of FIG. 17B, a recess 52y is provided in a lower surface 52x of the second rotating plate 52, and the desiccant 66 is housed in the recess 52y. Note that a perforated mesh lid 58 is provided at an opening edge of the recess 52y. The lid 58 prevents the desiccant 66 from falling by gravity.

According to this, when the rooms 44 to 47 are covered with the second rotating plate 52, the desiccant 66 can reduce the relative humidity in these rooms.

Moreover, when the rooms 44 to 47 are released to the atmosphere through the third opening 55 and the fourth opening 56 by rotating the second rotating plate 52, the desiccant 66 is trapped between the first and second rotating plates 51 and 52. Thus, when measurement using the QCM sensors 11a to 11d housed in the rooms 44 to 47 is started while exposing the QCM sensors to the atmosphere, a relative humidity around the QCM sensors 11a to 11d can be prevented from being lowered due to the desiccant 66.

Meanwhile, the first and second rotating shafts 51a and 52a are coaxial. The first rotating shaft 51a is mechanically connected to a first motor 61, and the second rotating shaft 52a is mechanically connected to a second motor 62.

Figure 18:
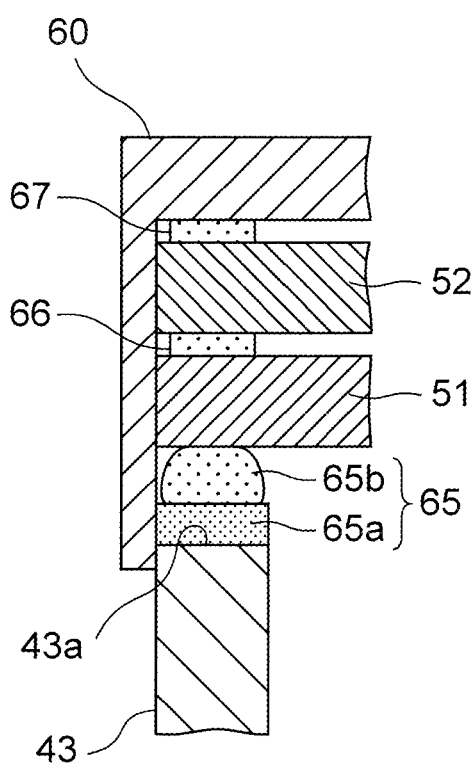
FIG. 18 is an enlarged cross-sectional view of an opening edge of a housing in the sensor unit according to the third embodiment.

FIG. 18 is an enlarged cross-sectional view of the opening edge 43a of the housing 43.

As illustrated in FIG. 18, first to third smoothing members 65 to 67 are provided at the edge of the cap 60 to increase airtightness in the first to fourth rooms 44 to 47.

Among them, the first smoothing member 65 has an elastic body 65a fixed to the opening edge 43a of the housing 43 and a seal material 65b fixed on the elastic body 65a. The elastic body 65a is sponge or rubber, for example, and elastically deforms itself to increase sticking force between the first smoothing member 65 and the first rotating plate 51.

Note that the elastic body 65a may be impregnated with a desiccant such as silica gel. Thus, the elastic body 65a has the same function as that of the desiccant 66 (see FIGS. 17A and 17B). Accordingly, the rooms 44 to 47 can be maintained at low relative humidity to prevent unnecessary corrosion of the electrodes 6 and 7 in the first to fourth QCM sensors 11a to 11d.

Moreover, the seal 65b contacts with the first rotating plate 51 to increase the airtightness in the first to fourth rooms 44 to 47. Also, the seal 65b reduces frictional force between the first smoothing member 65 and the first rotating plate 51 to smoothen the rotational movement of the first rotating plate 51.

The material of the seal 65b is not particularly limited. In this embodiment, silicon resin, fluorine resin or the like with good smoothness is used as the material of the seal 65b.

Meanwhile, the second smoothing member 66 is fixed to an upper surface of the first rotating plate 51 and is in contact with a rim of the second rotating plate 52 to reduce frictional force between the first and second rotating plates 51 and 52. Likewise, the third smoothing member 67 is fixed to the upper surface of the second rotating plate 52 to reduce frictional force between the second rotating plate 52 and the cap 60.

As the material of the second and third smoothing members 66 and 67, silicon resin, fluorine resin or the like can be used, for example.

Figure 19:
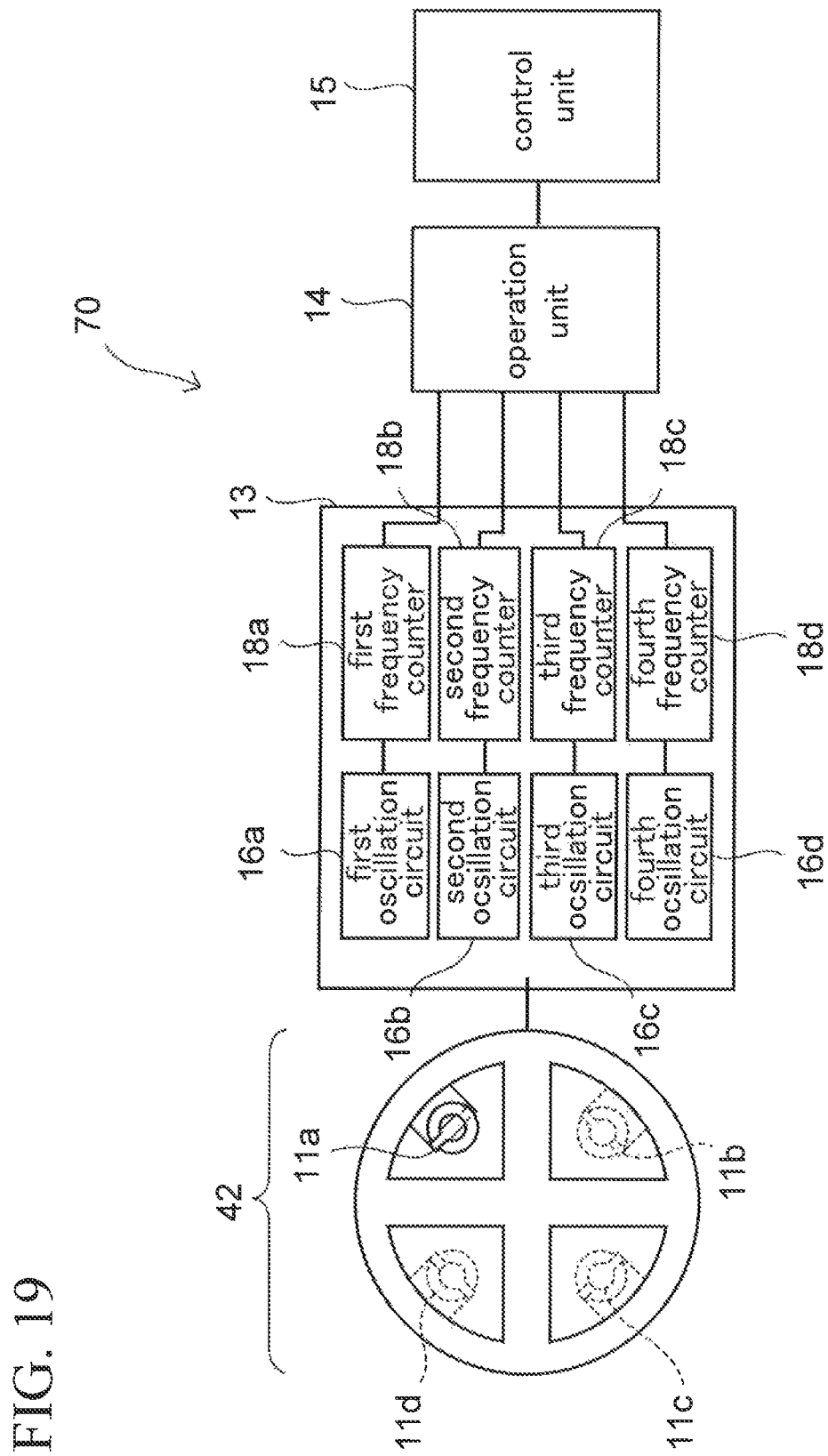
FIG. 19 is a configuration diagram of an environmental measurement apparatus according to the third embodiment.

FIG. 19 is a configuration diagram of an environmental measurement apparatus 70 including the sensor unit 42. Note that, in FIG. 19, the same components as those described with reference to FIG. 13 in the second embodiment are denoted by the same reference numerals as those in FIG. 13, and description thereof is omitted below.

As illustrated in FIG. 19, a drive unit 13 includes first to fourth oscillation circuits 16a to 16d and first to fourth frequency counters 18a to 18d corresponding to the first to fourth QCM sensors 11a to 11d, respectively.

Among them, the third and fourth oscillation circuits 16c and 16d are circuits to resonate the third and fourth QCM sensors 11c and 11d in a fundamental wave mode, and have the same circuit configuration as that illustrated in FIG. 4.

The third frequency counter 18c is connected to the third oscillation circuit 16c, and measures a third oscillation frequency $f_{3m}$ of the third QCM sensor 11c. Likewise, the fourth frequency counter 18d is connected to the fourth oscillation circuit 16d, and measures a fourth oscillation frequency $f_{4m}$ of the fourth QCM sensor 11d.

Furthermore, a control unit 15 to control rotation amounts of the first and second motors 61 and 62 (see FIG. 17A) is provided at the later stage of the operation unit 14.

Next, operations of the sensor unit 42 are described.

FIGS. 20A to 20C, 21A to 21C, and 22A to 22C are plan views for explaining the operations of the sensor unit 42.

Figure 20A:
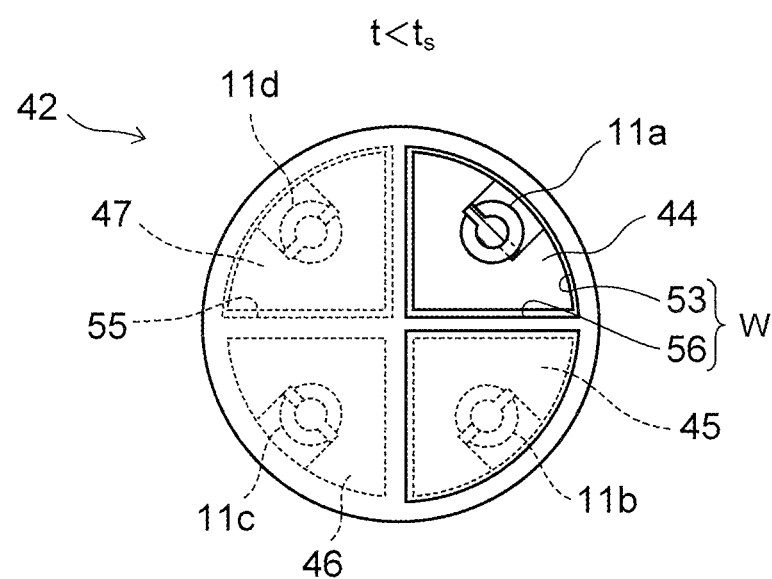
FIGS. 20A to 20C are diagrams illustrating states of the sensor unit at a time before a first time in the third embodiment.
Figure 20B:
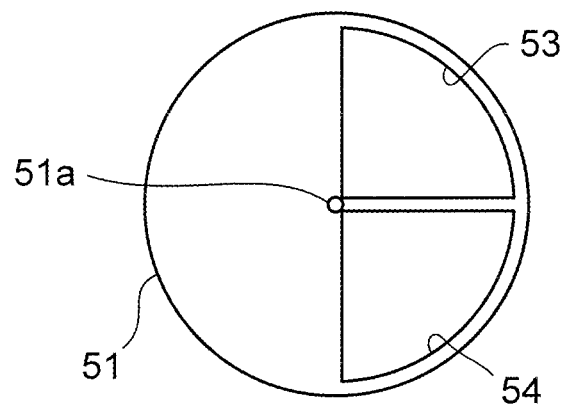
Figure 20C:
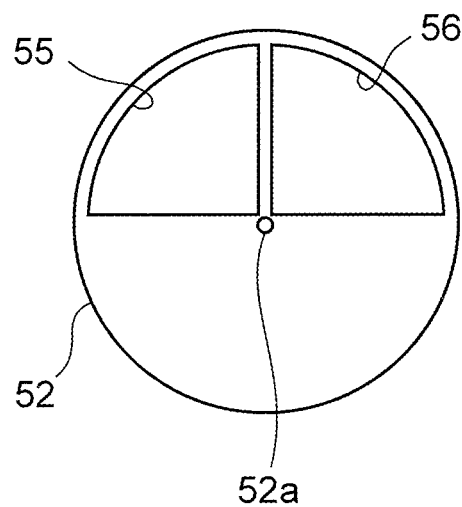

Among them, FIGS. 20A to 20C illustrate a state where a time t is before a first time $t_s$. FIG. 20A is a plan view of the sensor unit 42, FIG. 20B is a plan view of the first rotating plate 51, and FIG. 20C is a plan view of the second rotating plate 52.

At this time, as described in the first embodiment, the first QCM sensor 11a is not close to the end of its life yet, and the amount of corrosion caused by the corrosive gas is measured by using only the first QCM sensor 11a.

Thus, at this time, by adjusting the rotation amounts of the first and second rotating plates 51 and 52, the first opening 53 and the fourth opening 56 are overlaid over the first room 44 to form a window W by these openings, and the first QCM sensor 11a is exposed from the window W.

Also, in order to prevent corrosion of the electrodes 6 and 7 of new second to fourth QCM sensors 11b to 11d, the second to fourth rooms 45 to 47 are covered with at least one of the first and second rotating plates 51 and 52.

Figure 21A:
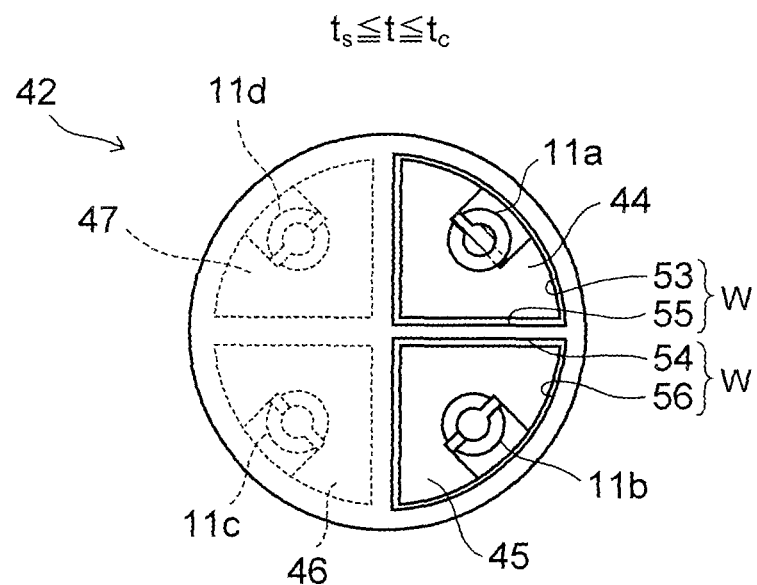
FIGS. 21A to 21C are diagrams illustrating states of the sensor unit at a time between the first time and a second time in the third embodiment.
Figure 21B:
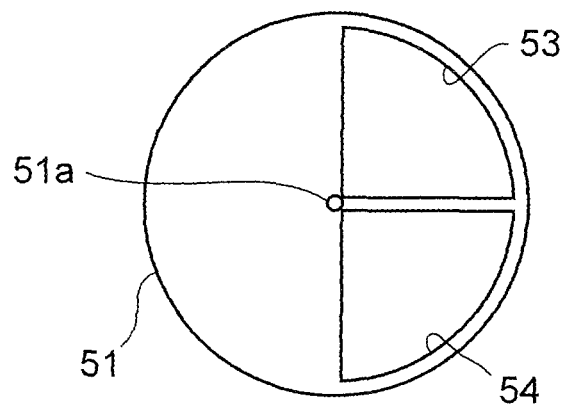
Figure 21C:
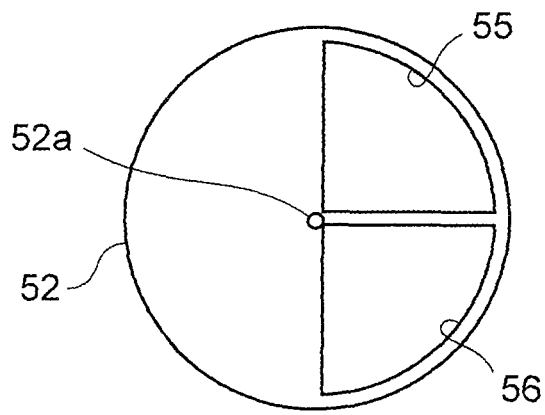

FIGS. 21A to 21C illustrate a state where the time t is between the first time $t_s$ and a second time $t_c$. FIG. 21A is a plan view of the sensor unit 42, FIG. 21B is a plan view of the first rotating plate 51, and FIG. 21C is a plan view of the second rotating plate 52.

Since this time is within a first period $T_1$ described in the first embodiment, correction is performed using both of the first and second QCM sensors 11a and 11b.

Thus, at this time, the first opening 53 and the third opening 55 are overlaid over the first room 44, and the second opening 54 and the fourth opening 56 are overlaid over the second room 45. Accordingly, windows W are formed by the first to fourth openings 53 to 56, and the first and second QCM sensors 11a and 11b are exposed from the windows W.

Note that the third and fourth rooms 46 and 47 are covered with the first and second rotating plates 51 and 52, in order to prevent corrosion of the electrodes 6 and 7 of the third and fourth QCM sensors 11c and 11d housed therein.

Figure 22A:
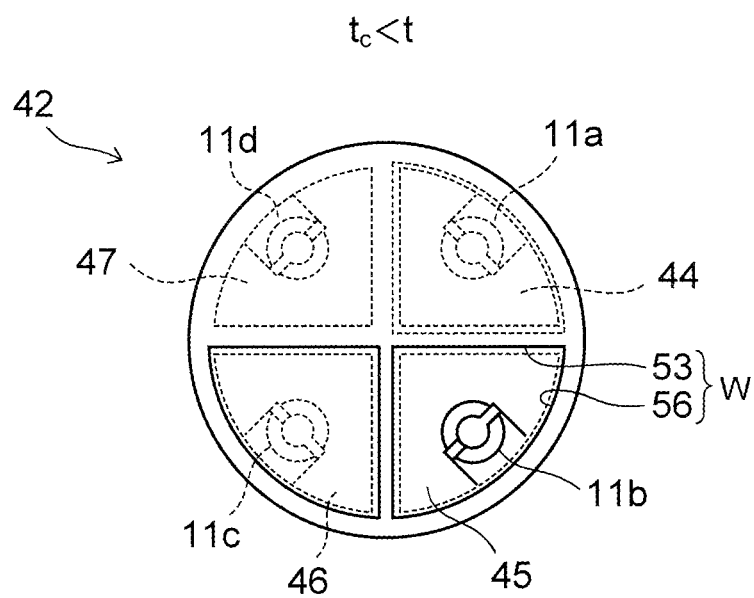
FIGS. 22A to 22C are diagrams illustrating states of the sensor unit at a time after the second time in the third embodiment.
Figure 22B:
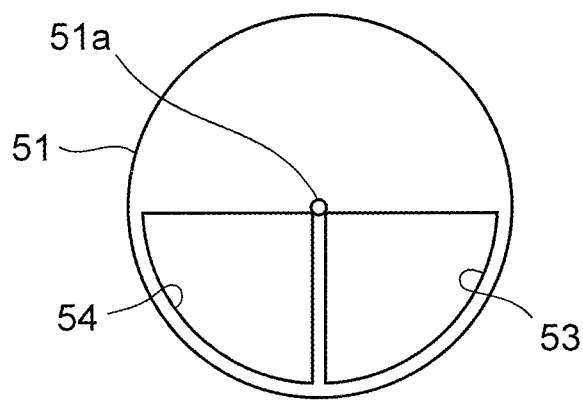
Figure 22C:
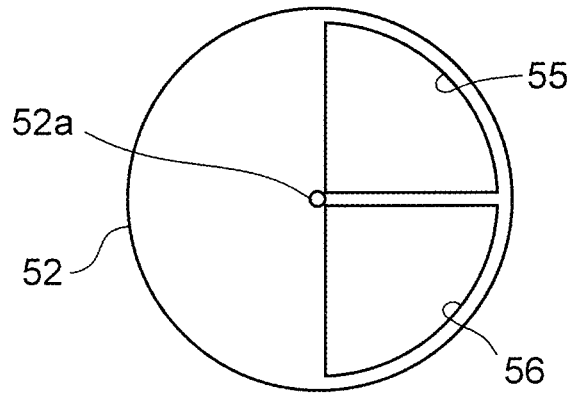

FIGS. 22A to 22C illustrate a state where the time t is after the second time $t_c$. FIG. 22A is a plan view of the sensor unit 42, FIG. 22B is a plan view of the first rotating plate 51, and FIG. 22C is a plan view of the second rotating plate 52.

At this time, as described in the first embodiment, the amount of corrosion is measured by using the new second QCM sensor 11b.

Thus, in this case, a window W is formed by overlaying the first opening 53 and the fourth opening 56 over the second room 45, and the second QCM sensor 11b is exposed from the window W.

Also, in order to prevent corrosion of the electrodes 6 and 7 of the new third and fourth QCM sensors 11c and 11d, the third and fourth rooms 46 and 47 are covered with at least one of the first and second rotating plates 51 and 52.

Furthermore, since there is no need to expose the first QCM sensor 11a that has come to the end of its life to the atmosphere, the first room 44 is covered with at least one of the first and second rotating plates 51 and 52.

Thereafter, when the life of the second QCM sensor 11b comes close to the end, the third QCM sensor 11c takes over the measurement. Furthermore, when the life of the third QCM sensor 11c comes close to the end, the fourth QCM sensor 11d takes over the measurement. A correction method during the taking over is the same as that in the first embodiment, and the movement of the rotating plates 51 and 52 is the same as those illustrated in FIGS. 20A to 20C, 21A to 21C, and 22A to 22C. Thus, description thereof is omitted.

According to this embodiment described above, as in the case of the second embodiment, it is automatically selected which one of the first to fourth QCM sensors 11a to 11d is to be exposed to the atmosphere. Thus, the burden of a user can be lessened.

Furthermore, the number of the QCM sensors that can be housed in one sensor unit 42 is four, which is larger than in the second embodiment. Thus, the corrosive gas in the atmosphere can be monitored over a longer time period by sequentially using the first to fourth QCM sensors 11a to 11d.

Fourth Embodiment

In the first embodiment, the first specified value $F_{sm}$ is used as a criterion for determining whether or not the life of the first QCM sensor 11a is close to the end in Step S2 as illustrated in FIG. 7.

The first specified value $F_{sm}$ is a specified value predetermined for the first change $\Delta f_{1m}$ in the first oscillation frequency $f_{1m}$ of the first QCM sensor 11a. Alternatively, the life of the first QCM sensor 11a may be determined as follows.

Figure 23:
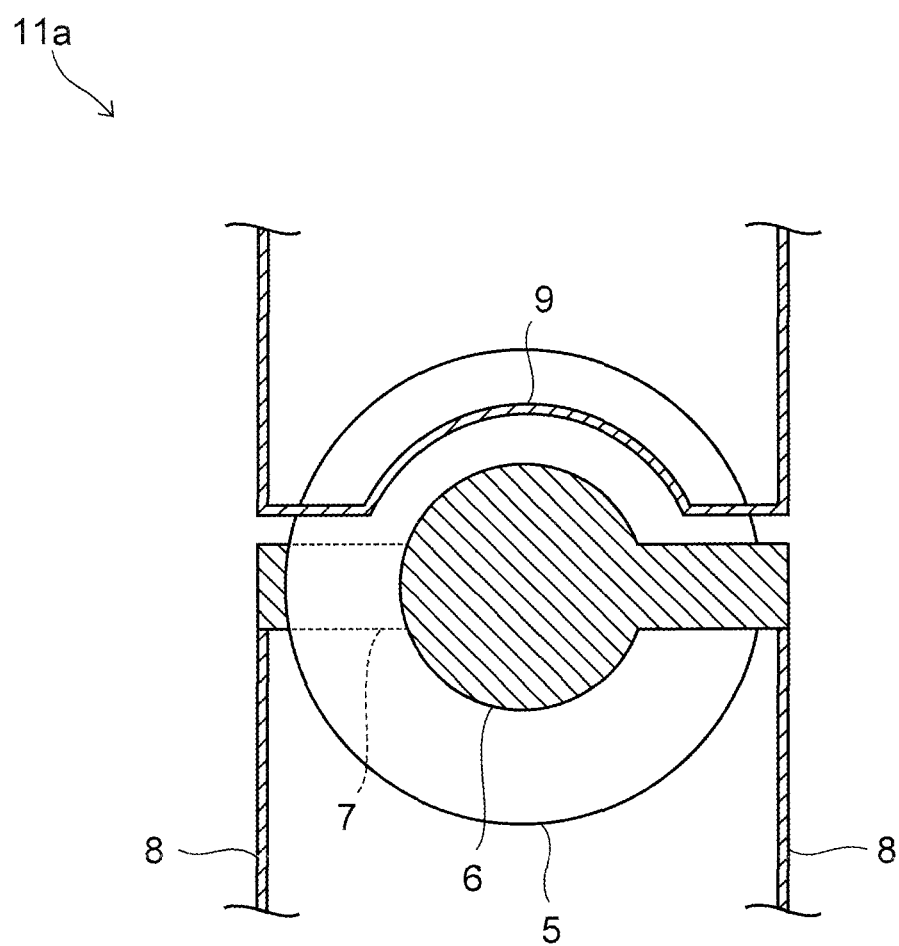
FIG. 23 is a plan view of a QCM sensor according to a fourth embodiment.

FIG. 23 is a plan view of a first QCM sensor 11a according to this embodiment. Note that, in FIG. 23, the same components as those described in the first embodiment are denoted by the same reference numerals as those in the first embodiment, and description thereof is omitted below.

As illustrated in FIG. 23, in this embodiment, a wire 9 independent of a first electrode 6 is provided on a main surface of a crystal oscillator 5, and an operation unit 14 (see FIG. 3) measures a resistance value R of a wire 9. Note that the wire 9 may be provided on another main surface of the crystal oscillator 5, which is opposite to the first electrode 6.

When the first QCM sensor 11a is placed in a corrosive gas atmosphere, not only the first electrode 6 but also the wire 9 is corroded, resulting in an increase in the resistance value R of the wire 9. Therefore, by monitoring the resistance value R of the wire 9, one can estimate how much of the first electrode 6 is corroded. Thus, it can be predicted whether the life of the first QCM sensor 11a is close to the end or not.

The material of the wire 9 is not particularly limited. However, it is preferable that the wire 9 is formed of the same material as that the corrosion is wished to be measured, such as silver or copper used as the material of the first electrode 6. By using the same material as that of the first electrode 6, the wire 9 and the first electrode 6 have the same corrosion rate. Thus, the life of the first QCM sensor 11a can be accurately predicted based on the resistance value R of the wire 9.

A processing method in Step S2 (see FIG. 7) in this embodiment is also not particularly limited. For example, a threshold value $R_1$ may be set for the resistance value R of the wire 9, and the operation unit 14 may determine in Step S2 whether or not the resistance value R is equal to or more than the threshold value $R_1$.

Here, when it is determined that the resistance value R is equal to or more than the threshold value $R_1$ (YES), the life of the first QCM sensor 11a is close to the end, and thus the processing goes to Step S3 according to the first embodiment. On the other hand, when it is determined that the resistance value R is not equal to or more than the threshold value $R_1$ (NO), the life of the first QCM sensor 11a is not close to the end yet, and thus the processing return to Step S1 as in the case of the first embodiment.

According to this embodiment described above, the life of the first QCM sensor 11a can be easily predicted by measuring the resistance value R of the wire 9 formed in the first QCM sensor 11a.

Fifth Embodiment

In this embodiment, QCM sensors are corrected by using a dedicated QCM sensor for correction as described below.

Figure 24:
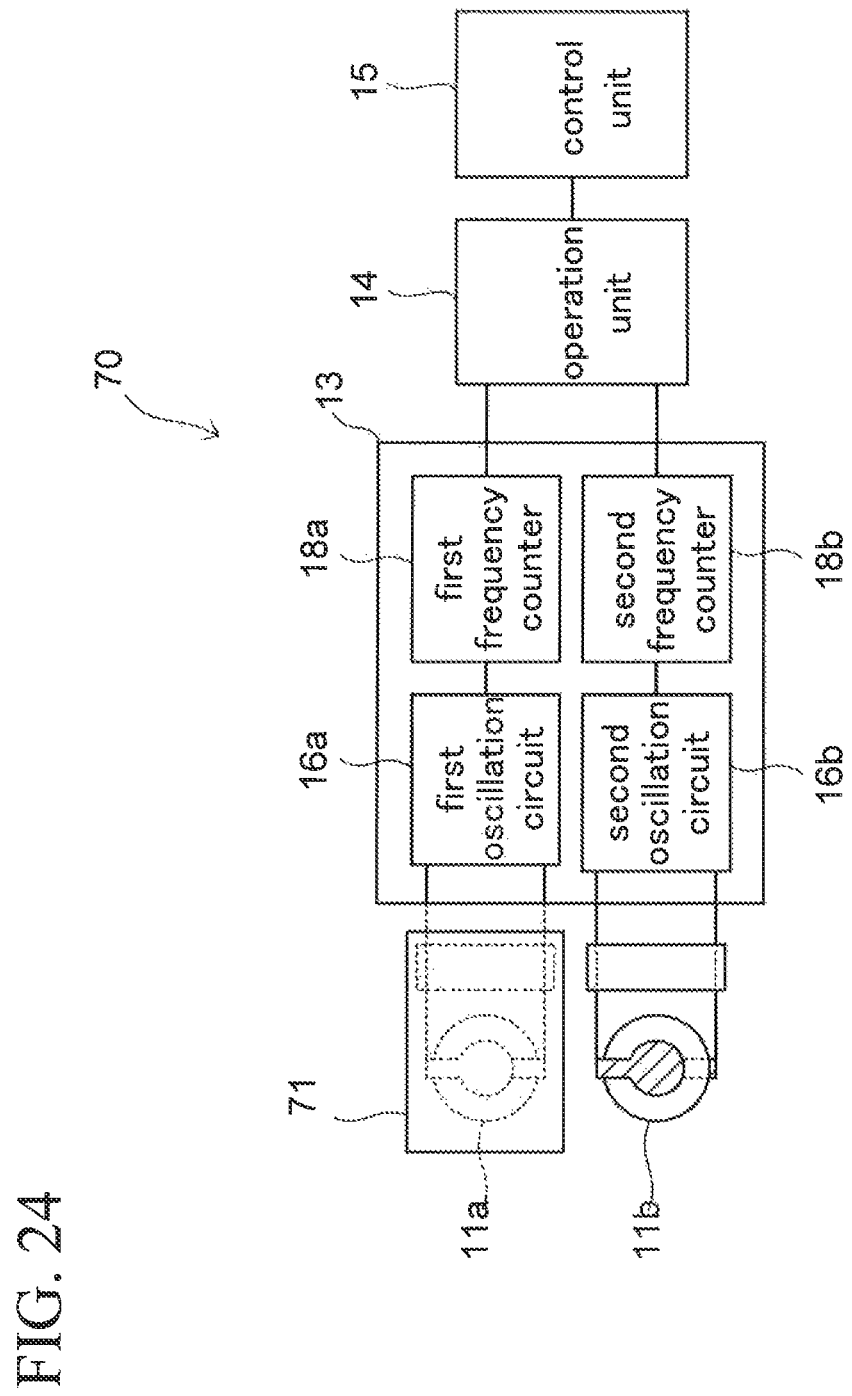
FIG. 24 is a configuration diagram of an environmental measurement apparatus according to a fifth embodiment.

FIG. 24 is a configuration diagram of an environmental measurement apparatus according to this embodiment. Note that, in FIG. 24, the same components as those described with reference to FIG. 3 are denoted by the same reference numerals as those in FIG. 3, and description thereof is omitted below.

As illustrated in FIG. 24, in the environmental measurement apparatus 70, a first QCM sensor 11a and a second QCM sensor 11b are attached to a drive unit 13 as in the case of the first embodiment.

The first QCM sensor 11a is the dedicated sensor for correction, and is housed in a sensor unit 71. The sensor unit 71 exposes the first QCM sensor 11a to the atmosphere only when performing correction as described later, and separates the first QCM sensor 11a from the atmosphere when performing no correction.

Meanwhile, the second QCM sensor 11b is used to monitor the amount of corrosion caused by a corrosive gas in the atmosphere, and is replaced with a new QCM sensor when the life thereof approaches the end.

Figure 25:
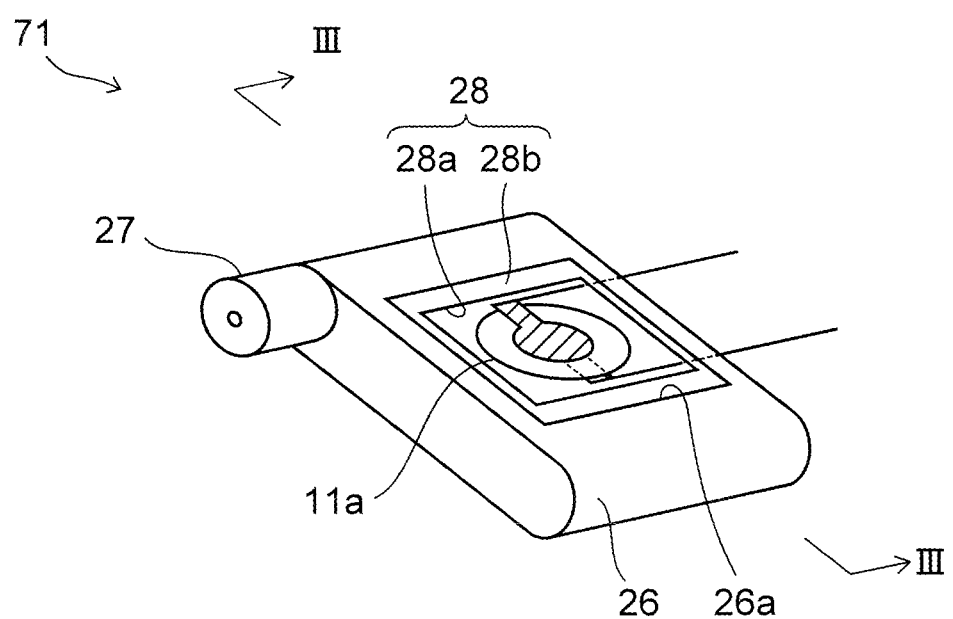
FIG. 25 is a perspective view of a sensor unit used in the fifth embodiment.

FIG. 25 is a perspective view of the sensor unit 71. Note that, in FIG. 25, the same components as those described with reference to FIGS. 10 to 12 are denoted by the same reference numerals as those in FIGS. 10 to 12, and description thereof is omitted below.

In the sensor unit 71, a shutter 28 is moved in a longitudinal direction thereof by rotation of a motor 27. By controlling the amount of movement of the shutter 28, the first QCM sensor 11a can be exposed from a window 28a of the shutter 28, and an opening 26a in a housing 26 can be covered with a shield portion 28b of the shutter 28.

Figure 26:
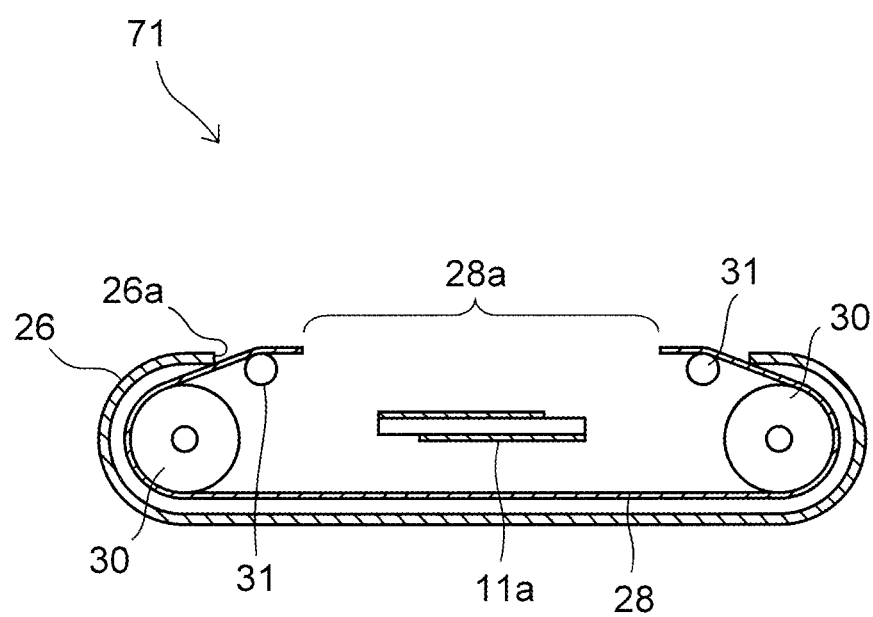
FIG. 26 is a cross-sectional view taken along the line III-III in FIG. 25.

FIG. 26 is a cross-sectional view taken along the line III-III in FIG. 25.

In this embodiment, only one first QCM sensor 11a is housed in the sensor unit 71. Therefore, the partition plate 32 as illustrated in FIG. 12 is not required, and only one room is defined in the housing 26.

Figure 27:
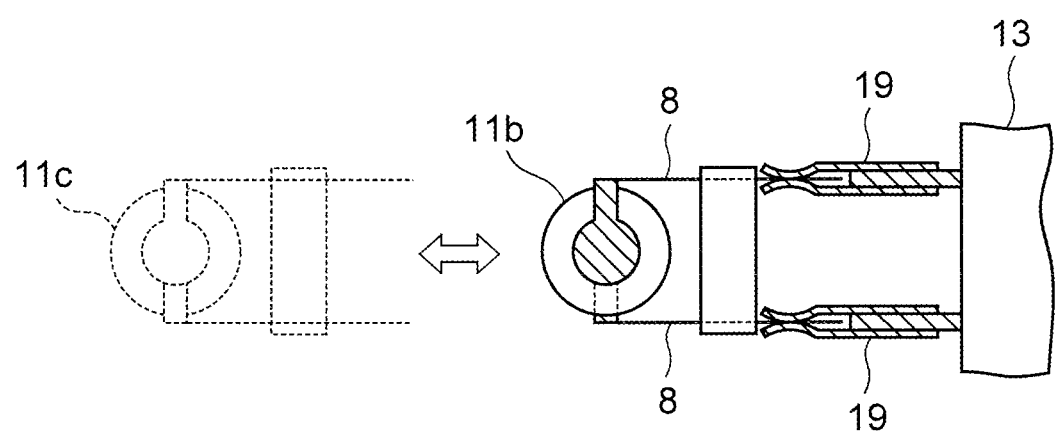
FIG. 27 is an enlarged view of a second QCM sensor and a drive unit in the fifth embodiment.

FIG. 27 is an enlarged view of the second QCM sensor 11b and the drive unit 13.

As illustrated in FIG. 27, the drive unit 13 is provided with two connectors 19, to and from which two conductive wires 8 in the second QCM sensor 11b can be attached and detached.

In this embodiment, when the second QCM sensor 11b comes to the end of its life, a user detaches the second QCM sensor 11b from the connectors 19 and attaches a new third QCM sensor 11c to the connectors 19.

The specifications of the first to third QCM sensors 11a to 11c are not particularly limited. However, in this embodiment, the first to third QCM sensors 11a to 11c have the same specifications, in order to accurately grasp variations in the amount of corrosion caused by the corrosive gas before and after the replacement of the old and new QCM sensors. Note that, as already mentioned, the specifications of the QCM sensors include the size and pane of the crystal oscillator 5, the size and material of each of the first and second electrodes 6 and 7, and the like, for example.

Next, an environmental measurement method according to this embodiment is described.

Figure 28:
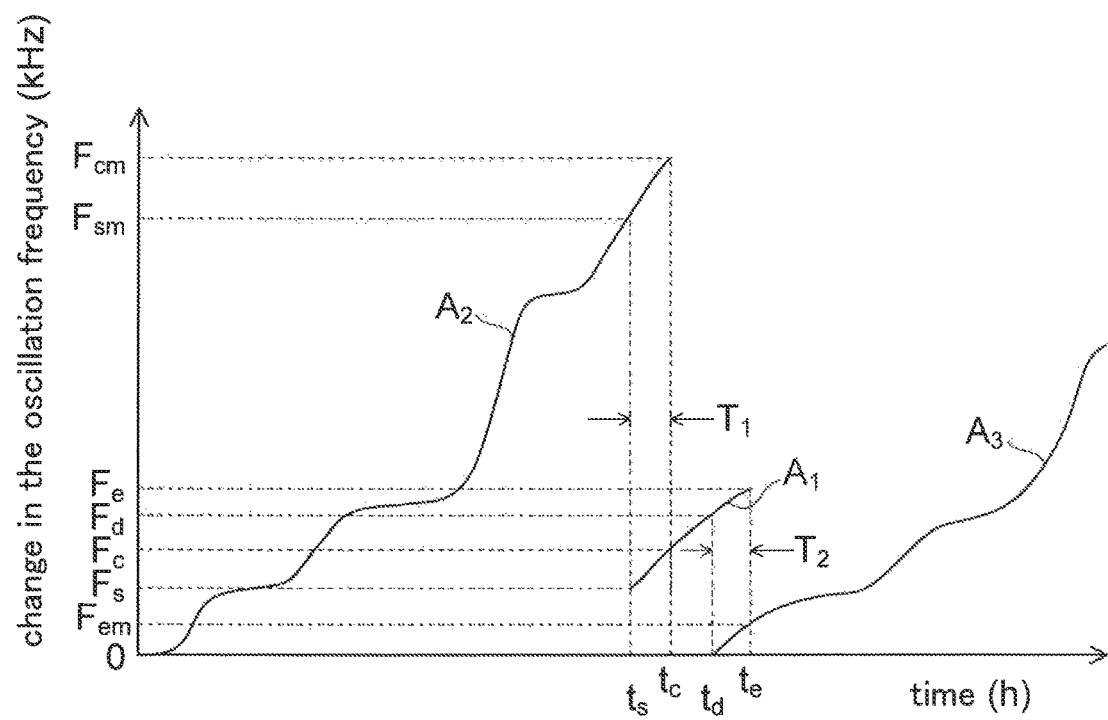
FIG. 28 is a graph illustrating an example of a result of measurement using QCM sensors according to the fifth embodiment.

FIG. 28 is a diagram illustrating an example of measurement results of the first to third QCM sensors 11a to 11c. In FIG. 28, first to third graphs $A_1$ to $A_3$ correspond to the measurement results of the first to third QCM sensors 11a to 11c, respectively.

The horizontal axis of each of the graphs represents time that has elapsed since the start of measurement with the second QCM sensor 11b. Also, the vertical axis of each graph represents first to third changes $\Delta f_{1m}$ to $\Delta f_{3m}$, which are changes in an oscillation frequency of each of the first to third QCM sensors 11a to 11c respectively.

Note that the third change $\Delta f_{3m}$ is defined by $\Delta f_{3m}=F_3-f_{3m}$ using a third oscillation frequency $f_{3m}$ of the third QCM sensor 11c. Here, $F_3$ is a fundamental frequency of the third QCM sensor 11c.

As illustrated in FIG. 28, in this embodiment, a second period $T_2$ is provided, during which the measurement is conducted with both of the first and third QCM sensors 11a and 11c, besides a first period $T_1$ during which the measurement is conducted with both of the first and second QCM sensors 11a and 11b.

A first time $t_s$, which is the beginning of the first period $T_1$, is the time when the second change $\Delta f_{2m}$ in the oscillation frequency of the second QCM sensor 11b reaches a predetermined first specified value $F_{sm}$. A second time $t_c$, which is the end of the first period $T_1$, is the time when the second change $\Delta f_{2m}$ reaches a predetermined second specified value $F_{cm}$.

A third time $t_d$, which is the beginning of the second period $T_2$, is the time to start acquiring the third oscillation frequency $f_{3m}$ of the third QCM sensor 11c. A fourth time $t_e$, which is the end of the second period $T_2$, is the time to end the acquisition of the first oscillation frequency $f_{1m}$ of the first QCM sensor 11a.

Here, since the first and second QCM sensors 11a and 11b have the same specifications as described above, the first and second graphs $A_1$ and $A_2$ are expected to have the same slope during the first period $T_1$. However, the individual difference of the first and second QCM sensors 11a and 11b actually cause a difference in slope between the graphs $A_1$ and $A_2$ during the first period $T_1$ as illustrated in FIG. 28.

For the same reason, the first and third graphs $A_1$ and $A_3$ have different slopes during the second period $T_2$.

In order to prevent inaccurate results of measurement of the amount of corrosion caused by the corrosive gas in the atmosphere due to such individual difference, the measurement values of the second and third QCM sensors 11b and 11c are corrected as follows in this embodiment.

Figure 29:
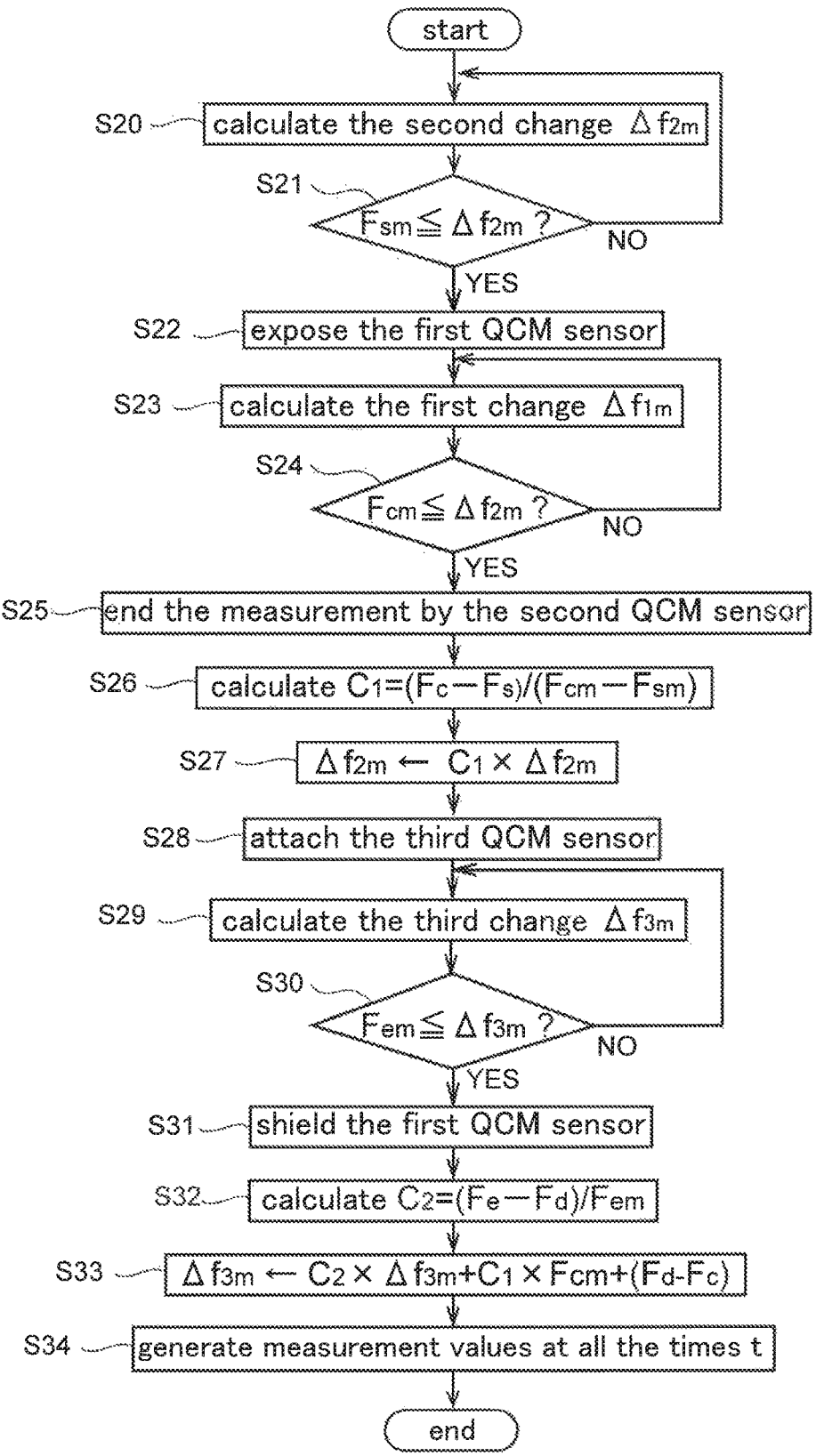
FIG. 29 is a flowchart for explaining an environmental measurement method according to the fifth embodiment.

FIG. 29 is a flowchart for explaining an environmental measurement method according to this embodiment.

In the first Step S20, an operation unit 14 acquires the second oscillation frequency $f_{2m}$ of the second QCM sensor 11b at a time t, and calculates the second change $\Delta f_{2m}$ in the oscillation frequency $f_{2m}$ at the time t. The second change $\Delta f_{2m}$ is a difference $(F_2-f_{2m})$ between the fundamental frequency $F_2$ which is the oscillation frequency of the second QCM sensor 11b at a time 0 and the second oscillation frequency $f_{2m}$ at the time t.

Next, in Step S21, the operation unit 14 determines whether or not the second change $\Delta f_{2m}$ is equal to or more than the first specified value $F_{sm}$.

Here, when it is determined that the second change $\Delta f_{2m}$ is not equal to or more than the first specified value $F_{sm}$ (NO), the second QCM sensor 11b is considered to be not close to the end of its life yet. Thus, the processing returns to Step S20 to continue the measurement using the second QCM sensor 11b.

On the other hand, when it is determined in Step S21 that the second change $\Delta f_{2m}$ is equal to or more than the first specified value $F_{sm}$ (YES), it is considered that the time t is within the first period $T_1$ described above and the life of the second QCM sensor 11b is coming close to the end.

Therefore, in this case, the processing goes to Step S22 to prepare for correction using the first QCM sensor 11a by driving the motor 27 (see FIG. 25) under the control of a control unit 15 to move the shutter 28 and exposing the first QCM sensor 11a from the window 28a.

Next, in Step S23, the operation unit 14 starts acquiring the first oscillation frequency $f_{1m}$ of the first QCM sensor 11a. Considering the time needed for moving the shutter 28 (see FIG. 25), the start time is slightly behind the first time $t_s$. However, the acquisition of the first oscillation frequency $f_{1m}$ is substantially started from the first time $t_s$.

Then, the operation unit 14 starts calculating the first change $\Delta f_{1m}$ in the first oscillation frequency $f_{1m}$ at the time t. The first change $\Delta f_{1m}$ is a difference $(F_1-f_{1m})$ between the fundamental frequency $F_1$ which is the oscillation frequency of the first QCM sensor 11a at the first time $t_s$ and the first oscillation frequency $f_{1m}$ at the time t.

Next, in Step S24, the operation unit 14 determines whether or not the first change $\Delta f_{1m}$ is equal to or more than the second specified value $F_{cm}$ described above.

Here, when it is determined that the first change $\Delta f_{1m}$ is not equal to or more than the second specified value $F_{cm}$ (NO), it is considered that the life of the second QCM sensor 11b is approaching the end but does not yet reach the end. Thus, the processing returns to Step S23.

On the other hand, when it is determined in Step S24 that the first change $\Delta f_{1m}$ is equal to or more than the second specified value $F_{cm}$ (YES), it is considered that the second QCM sensor 11b come to the end of its life.

Thus, in this case, the processing goes to Step S25 to end the measurement carried out by the second QCM sensor 11b at the second time $t_c$, at which the second change $\Delta f_{2m}$ becomes equal to the second specified value $F_{cm}$.

Thereafter, in Step S26, the operation unit 14 calculates a first correction coefficient $C_1$ to retrospectively correct the second change $\Delta f_{2m}$ at or before the second time $t_c$.

Figure 30:
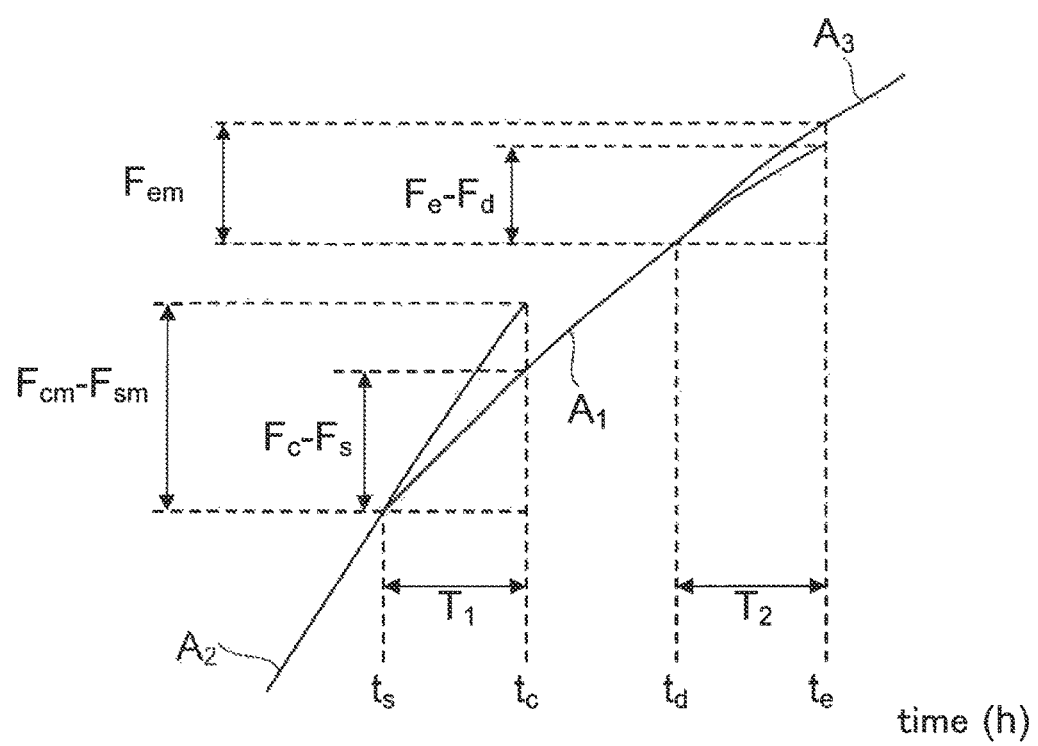
FIG. 30 is a diagram for explaining a method for calculating a first correction coefficient in the fifth embodiment.

FIG. 30 is a diagram for explaining a method for calculating the first correction coefficient $C_1$. In FIG. 30, the first graph $A_1$ illustrated in FIG. 28 is subjected to an upward parallel translation, thereby matching the starting point of the first graph $A_1$ with the second graph $A_2$ at the first time $t_s$.

Moreover, the third graph $A_3$ is also subjected to an upward parallel translation to match the starting point thereof with the first graph $A_1$ at the third time $t_d$.

Due to differences in slope among the first to third graphs $A_1$ to $A_3$, mere parallel translation like this cannot connect each graphs.

In this step, in order to resolve such a difference in slope between the first and second graphs $A_1$ and $A_2$ among the graphs, the operation unit 14 calculates the first correction coefficient $C_1$ by which the second change $\Delta f_{2m}$ is to be multiplied as follows.

First, a first increment $F_c-F_s$ of the first change $\Delta f_{1m}$ within the first period $T_1$ and a second increment $F_{cm}-F_{sm}$ of the second change $\Delta f_{2m}$ within the first period $T_1$ are calculated. Note that $F_s$ is the value of the first change $\Delta f_{1m}$ at the first time $t_s$, and $F_c$ is the value of the first change $\Delta f_{1m}$ at the second time $t_c$.

Then, the operation unit 14 calculates a first ratio $(F_c-F_s)/(F_{cm}-F_{sm})$ of the first increment $F_c-F_s$ to the second increment $F_{cm}-F_{sm}$, and sets the first ratio as the first correction coefficient $C_1$. The first correction coefficient $C_1$ thus calculated is equal to a ratio between the slopes of the second and first graphs $A_2$ and $A_1$ in FIG. 28 during the first period $T_1$.

Then, in Step S27, the operation unit 14 retrospectively corrects the already calculated second change $\Delta f_{2m}$ by multiplying the second change $\Delta f_{2m}$ at or before the first time $t_s$ by the first correction coefficient $C_1$.

As described above, the first correction coefficient $C_1$ is equal to the ratio between the slopes of the graphs $A_1$ and $A_2$. Therefore, by multiplying the second change $\Delta f_{2m}$ by the first correction coefficient $C_1$ in this step, the graph $A_2$ can be corrected to match the slope thereof with the slope of the graph $A_1$.

Moreover, during the first period $T_1$, the corrosion of the second QCM sensor 11b progresses considerably and thus the slope of the second graph $A_2$ is stabilized. As a result, errors are less likely to occur in the second increment $F_{cm}-F_{sm}$, and the second change $\Delta f_{2m}$ can be accurately corrected in this step.

Next, in Step S28, the user detaches the second QCM sensor 11b from the connectors 19 (see FIG. 27), and attaches a new third QCM sensor 11c to the connectors 19.

Then, in Step S29, the operation unit 14 starts acquiring the third oscillation frequency $f_{3m}$ of the third QCM sensor 11c at the third time $t_d$, and calculates the third change $\Delta f_{3m}$ in the third oscillation frequency $f_{3m}$ at the time t.

As already mentioned, the third change $\Delta f_{3m}$ at the time t is defined by $\Delta f_{3m}=F_3-f_{3m}$ using the fundamental frequency $F_3$ of the third QCM sensor 11c and the third oscillation frequency $f_{3m}$ at the time t.

Thereafter, in Step S30, the operation unit 14 determines whether or not the third change $\Delta f_{3m}$ is equal to or more than the predetermined third specified value $F_{em}$.

The third specified value $F_{em}$ is served as the clue to determine whether one can obtain the third change $\Delta f_{3m}$ which is large enough to correct the third QCM sensor 11c, and is preset by the user. Moreover, as presented in FIG. 30, the third specified value $F_{em}$ also has a meaning of an increment of the third graph $A_3$ during the second period $T_2$, i.e., a third increment of the third change $\Delta f_{3m}$.

Here, when it is determined that the third change $\Delta f_{3m}$ is not equal to or more than the third specified value $F_{em}$ (NO), since the magnitude of the third change $\Delta f_{3m}$ is not sufficient yet, the processing returns to Step S29 again.

On the other hand, when it is determined in Step S30 that the third change $\Delta f_{3m}$ is equal to or more than the third specified value $F_{em}$ (YES), the processing goes to Step S31. In Step S31, the motor 27 (see FIG. 25) is driven under the control of the control unit 15 to move the shutter 28, and the first QCM sensor 11a is shielded with the shield portion 28b of the shutter 28.

Accordingly, the acquisition of the first oscillation frequency $f_{1m}$ of the first QCM sensor 11a, which has started in Step S23, is completed.

Moreover, by covering the opening 26a with the shutter 28 in this manner, the electrodes 6 and 7 in the first QCM sensor 11a can be separated from the outside air. As a result, the progress of the corrosion of the electrodes 6 and 7 due to the corrosive gas contained in the outside air is stopped. Thus, the life of the first QCM sensor 11a can be extended.

Next, the processing goes to Step S32. In Step S32, as illustrated in FIG. 30, the operation unit 14 calculates a first increment $F_e-F_d$ of the first change $\Delta f_{1m}$ within the second period $T_2$ and a third increment $F_{em}$ of the third change $\Delta f_{3m}$ within the second period $T_2$.

Furthermore, the operation unit 14 calculates a second ratio $(F_e-F_d)/F_{em}$ of the first increment $F_e-F_d$ to the third increment $F_{em}$, and sets the second ratio as a second correction coefficient $C_2$. The second correction coefficient $C_2$ thus calculated is equal to a ratio between the slopes of the first and third graphs $A_1$ and $A_3$ in FIG. 28 during the second period $T_2$.

Then, in Step S33, the operation unit 14 corrects the third change $\Delta f_{3m}$ by multiplying the third change $\Delta f_{3m}$ at and after the third time $t_d$ by the second correction coefficient $C_2$.

As described above, the second correction coefficient $C_2$ is equal to the ratio between the slopes of the graphs $A_1$ and $A_3$. Therefore, by multiplying the third change $\Delta f_{3m}$ by the second correction coefficient $C_2$ in this step, the graph $A_3$ can be corrected to match the slope thereof with the slope of the graph $A_1$.

Furthermore, in order to match the height of the third graph $A_3$ with that of the corrected first graph $A_1$, the operation unit 14 further corrects the third change $\Delta f_{3m}$ as indicated by the following equation (2).

$$\Delta f_{3m} \leftarrow C_2 \times \Delta f_{3m} + C_1 \times F_{cm} + (F_d - F_c) \quad (2)$$

The second term in the right-hand side of the equation (2) is the value of the second graph $A_2$ at the second time $t_c$, which is corrected in Step S27. The third term in the right-hand side is an increment of the first graph $A_1$ between the second time $t_c$ and the third time $t_d$. By adding these two terms to the corrected value $(C_2 \times \Delta f_{3m})$ described above, the height of the third graph $A_3$ can be matched with that of the corrected first graph $A_1$ while taking into consideration the increment of the first graph $A_1$.

Next, in Step S34, the operation unit 14 uses the correction values calculated in Steps S27 and S33 described above to generate measurement values at all the times t as follows.

First, when the time t is before the second time $t_c$, the value $(C_1 \times \Delta f_{2m})$ calculated in Step S27 is used as the measurement value at the time t.

When the time t is between the second time $t_c$ and the third time $t_d$, $\Delta f_{1m}+C_1 \times F_{cm}$ is used as the measurement value.

When the time t is after the third time $t_d$, the corrected value $(C_2 \times \Delta f_{3m}+C_1 \times F_{cm}+(F_d-F_c))$ of equation (2) is used as the measurement value.

Figure 31:
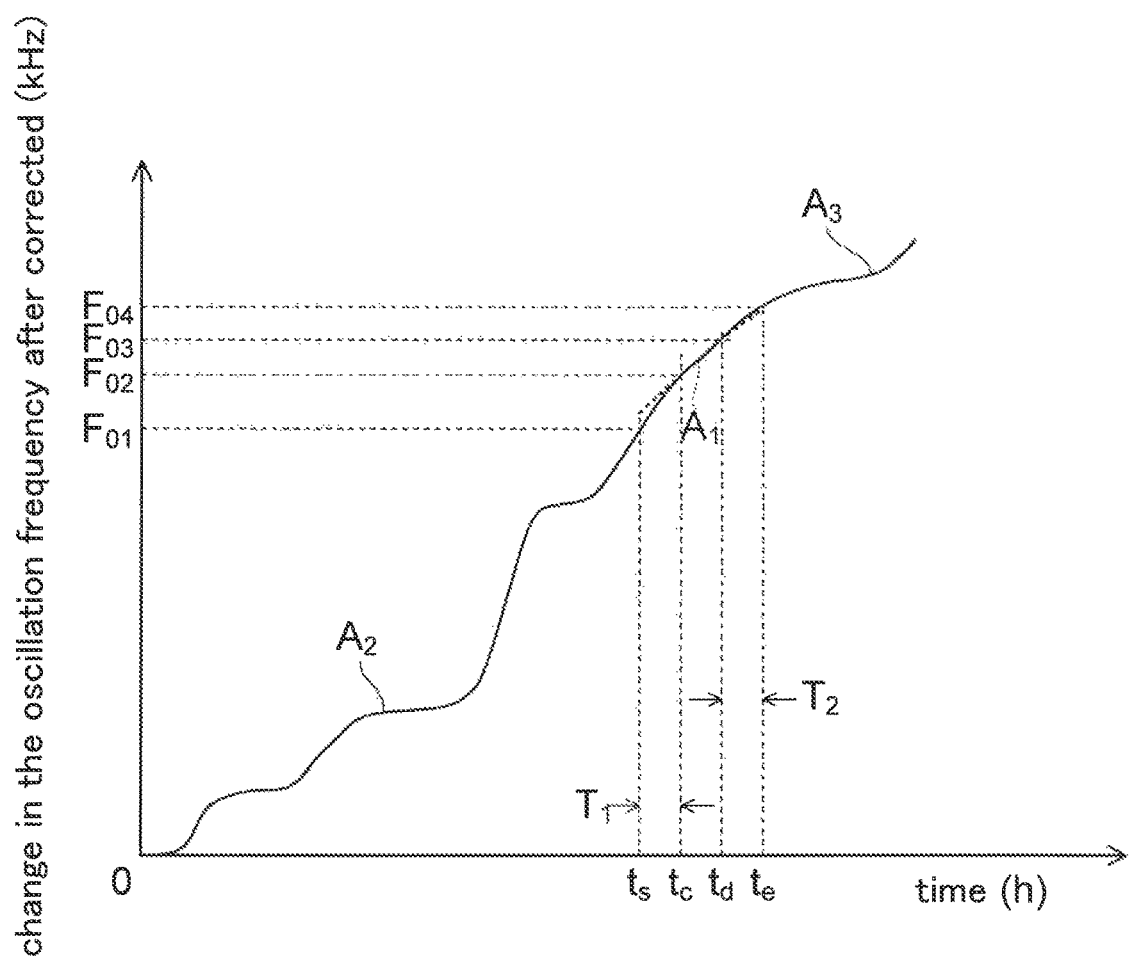
FIG. 31 is a graph obtained from measurement values generated in the fifth embodiment.

FIG. 31 is a graph obtained by the measurement values generated in this step. Note that the horizontal axis and vertical axis of this graph mean the same as those described with reference to FIG. 28, and thus description thereof is omitted here.

In FIG. 31, portions corresponding to the first to third graphs $A_1$ to $A_3$ before the correction are denoted by reference numerals $A_1$ to $A_3$. Also, $F_{01}$ to $F_{04}$ represent values of the graphs corresponding to the first to fourth times $t_s$ to $t_e$.

As illustrated in FIG. 31, the measurement values can be continuously acquired throughout the all times t by performing the correction as described above.

Figure 32:
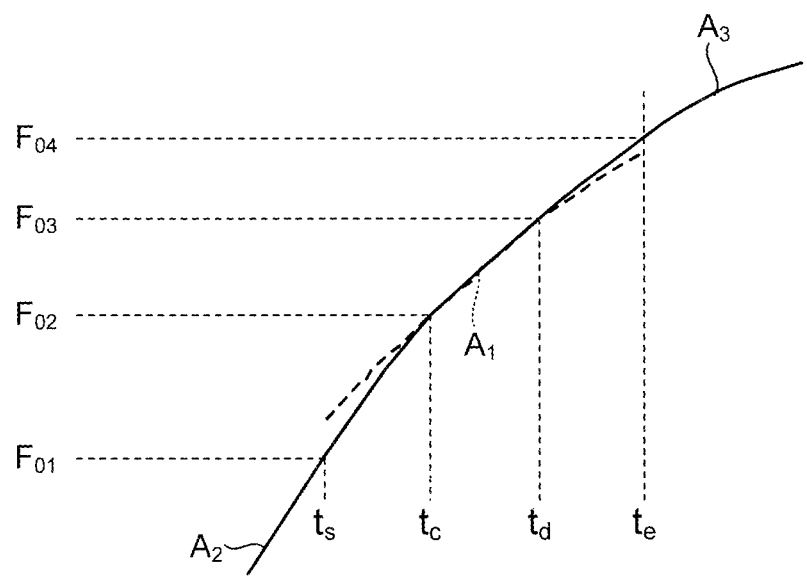
FIG. 32 is an enlarged view of the graph in FIG. 31.

FIG. 32 is an enlarged view of the graph illustrated in FIG. 31 at the first to fourth times $t_s$ to $t_e$.

As illustrated in FIG. 32, the graphs at the first to fourth times $t_s$ to $t_e$ are smoothly connected by the above correction.

Thus, the basic steps of the environmental measurement method according to this embodiment are completed.

According to this embodiment described above, the first QCM sensor 11a is used as the dedicated sensor for correction. Thus, the measurement values can be continuously acquired throughout the all times t as illustrated in FIG. 31 by correcting the second change $\Delta f_{2m}$ of the second QCM sensor 11b and the third change $\Delta f_{3m}$ of the third QCM sensor 11c.

Moreover, the life of the first QCM sensor 11b can also be extended by using the first QCM sensor 11b only for the purpose of correction and separating the first QCM sensor 11b from the atmosphere when performing no correction.

Furthermore, the first QCM sensor 11b used only for correction is exposed to the atmosphere every time the correction is performed, and hence the corrosion of the electrodes 6 and 7 progresses to some extent. Therefore, the characteristics of the first QCM sensor 11b are stabilized as in the case of performing the aging treatment. Accordingly, the correction accuracy is improved by correcting the second change $\Delta f_{2m}$ and the third change $\Delta f_{3m}$ based on the first QCM sensor 11b as in this embodiment.

Sixth Embodiment

In the fifth embodiment, the user replaces the second QCM sensor 11b, whose life has come to the end, with the new third QCM sensor 11c by user's own hand in Step S28 of FIG. 29. In this embodiment, the replacement is automatically performed as follows.

Figure 33:
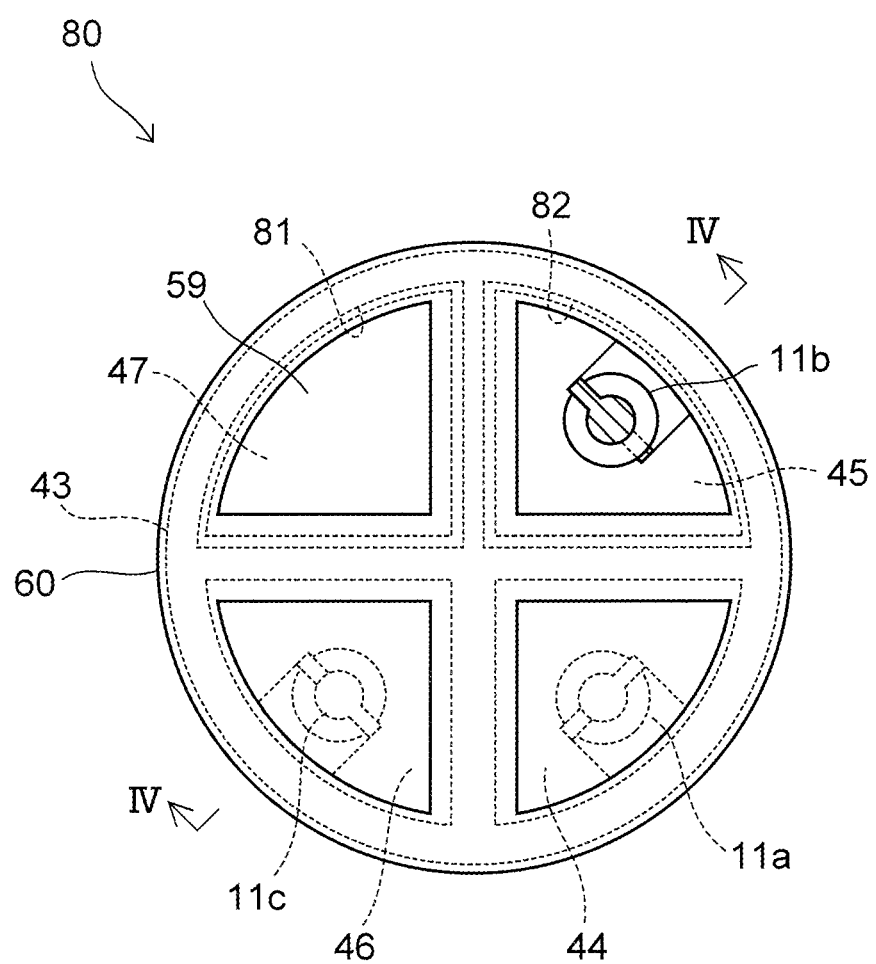
FIG. 33 is a plan view of a sensor unit used in a sixth embodiment.

FIG. 33 is a plan view of a sensor unit 80 used in this embodiment. Note that, in FIG. 33, the same components as those described with reference to FIG. 15 are denoted by the same reference numerals as those in FIG. 15, and description thereof is omitted below.

The sensor unit 80 includes a housing 43 having a cylindrical shape in a planar view, a circular shutter 59 made of resin or metal, and a cap 60 covering the shutter 59.

In the housing 43, first to fourth rooms 44 to 47 are provided.

The positions of the rooms are not particularly limited. In this embodiment, the second room 45 is provided on one of the sides of the first room 44, and the third room 46 is provided on the other side thereof. Also, the fourth room 47 is provided adjacent to both of the second room 45 and the third room 46.

The first to third QCM sensors 11a to 11c are housed in the first to third rooms 44 to 46, respectively. Note that no QCM sensor is housed in the fourth room 47 in this embodiment.

Although the shutter 59 includes the two rotating plates 51 and 52 as illustrated in FIG. 15 in the third embodiment, the shutter 59 of this embodiment includes only one rotating plate.

Figure 34:
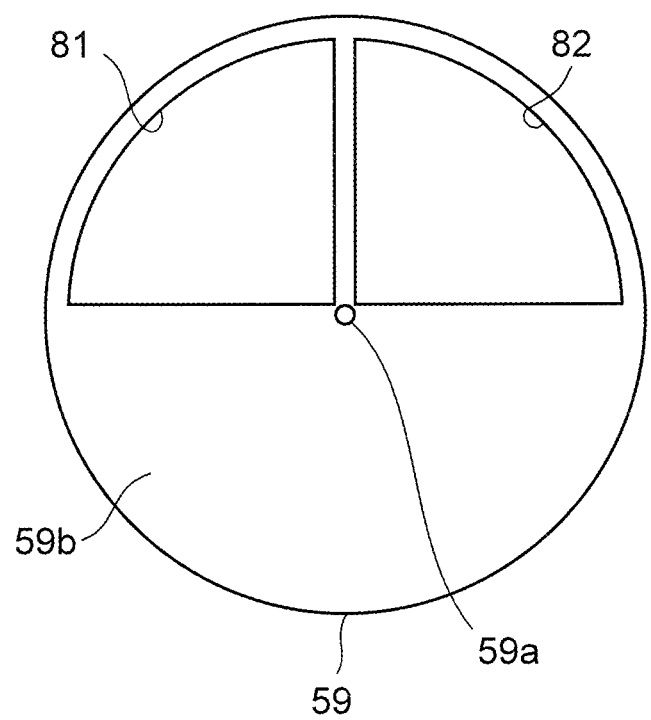
FIG. 34 is a plan view of a shutter included in the sensor unit used in the sixth embodiment.

FIG. 34 is a plan view of the shutter 59.

As illustrated in FIG. 34, the shutter 59 has a circular shape in the planar view, and can rotate about a shaft 59a. Moreover, a first window 81 and a second window 82 are formed in the shutter 59. A portion of the shutter 59, in which the windows are not formed, is served as a shield portion 59b to cover the first to fourth rooms 44 to 47.

The first and second windows 81 and 82 are formed so as to correspond to two adjacent rooms of the first to fourth rooms 44 to 47. Thus, two adjacent rooms selected from the first to fourth rooms 44 to 47 communicate with the first and second windows 81 and 82, and the remaining non-selected rooms are covered with the shield portion 59b.

Figure 35:
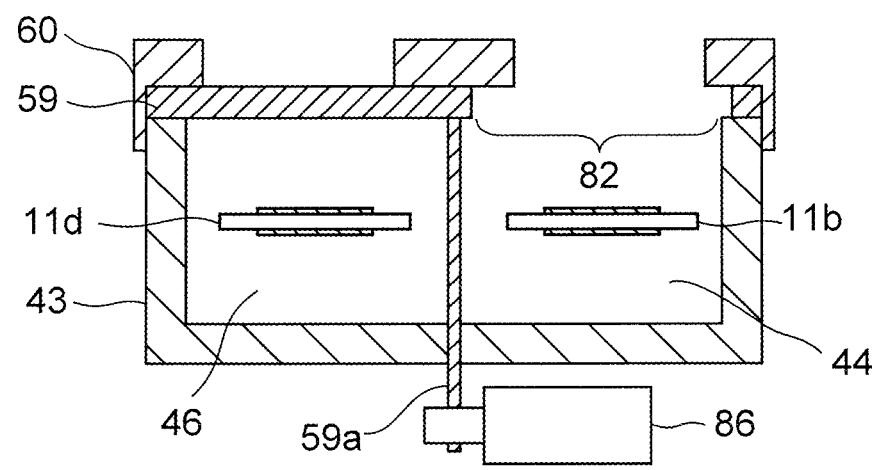
FIG. 35 is a cross-sectional view taken along the line IV-IV in FIG. 33.

FIG. 35 is a cross-sectional view taken along the line IV-IV in FIG. 33.

The cap 60 has an inner side surface mechanically fixed to an outer peripheral side surface of the housing 43. The cap 60 slides on an upper surface of the shutter 59, thereby suppressing rattling of the shutter 59.

Meanwhile, the shaft 59a is mechanically connected to a motor 86, and can rotate the shutter 59 by rotation of the motor 86.

Note that a desiccant 66 (see FIGS. 17A and 17B) described in the third embodiment may be placed in each of the rooms 44 to 46 to prevent corrosion of electrodes 6 and 7 in the first to third QCM sensors 11a to 11c from being promoted by moisture.

Figure 36:
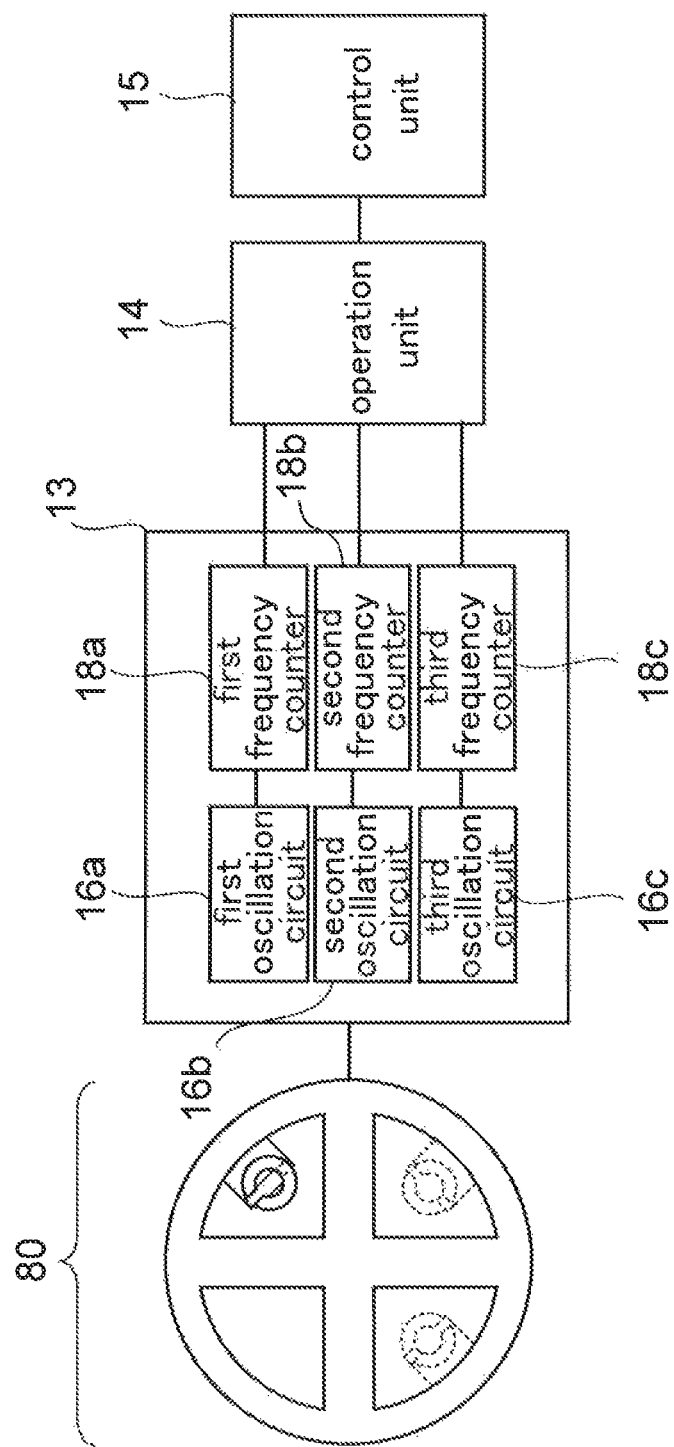
FIG. 36 is a configuration diagram of an environmental measurement apparatus according to the sixth embodiment.

FIG. 36 is a configuration diagram of an environmental measurement apparatus including the sensor unit 80. Note that, in FIG. 36, the same components as those described with reference to FIGS. 19, 20A to 20C, 21A to 21C, 22A to 22C, 23 and 24 are denoted by the same reference numerals as those in these figures, and description thereof is omitted below.

As illustrated in FIG. 36, the first to third QCM sensors 11a to 11c in the sensor unit 80 are connected to a control unit 15 through a drive unit 13 and an operation unit 14. In this embodiment, the control unit 15 adjusts a rotation amount of the shutter 59 by controlling a rotation amount of the motor 86.

Next, operations of the sensor unit 80 are described.

FIGS. 37A to 37D are plan views for explaining the operations of the sensor unit 80.

FIG. 37A illustrates a state where the time t is before the first time $t_s$. At this time, as described in the fifth embodiment, the second QCM sensor 11b is not close to the end of its life yet, and the amount of corrosion caused by a corrosive gas is measured by using only the second QCM sensor 11b.

Thus, at this time, the second window 82 communicates with the second room 45 by adjusting the rotation amount of the shutter 59, and the second QCM sensor 11b is exposed from the second window 82.

Moreover, in order to prevent the corrosion of the electrodes 6 and 7 in the first QCM sensor 11a for correction and the new third QCM sensor 11c, the first and third rooms 44 and 46 are covered with the shield portion 59b.

FIG. 37B illustrates a state where the time t is between the first time $t_s$ and the second time $t_e$.

Since this time is within the first period $T_1$ described in the fifth embodiment, correction is performed using both of the first and second QCM sensors 11a and 11b.

Therefore, at this time, the first and second QCM sensors 11a and 11b are exposed from the windows 81 and 82 by communicating the second opening 82 with the first room 44 and communicating the first opening 81 with the second room 45.

Note that the third room 46 is covered with the shield portion 59b to prevent the corrosion of the electrodes 6 and 7 in the third QCM sensor 11c housed therein.

FIG. 37C illustrates a state where the time t is between the third time $t_d$ and the fourth time $t_e$.

Since this time is within the second period $T_2$ described in the fifth embodiment, correction is performed using both of the first and third QCM sensors 11a and 11c.

Therefore, at this time, the first and third QCM sensors 11a and 11c are exposed from the windows 81 and 82 by communicating the first opening 81 with the first room 44 and communicating the second opening 82 with the third room 46.

Furthermore, since there is no need to expose the second QCM sensor 11b that has come to the end of its life to the atmosphere, the second room 45 is covered with the shield portion 59b.

FIG. 37D illustrates a state where the time t is after the fourth time $t_e$.

At this time, as described in the fifth embodiment, the amount of corrosion caused by the corrosive gas is measured by using only the third QCM sensor 11c. Therefore, in this case, the third QCM sensor 11c is exposed from the first window 81 by communicating the first window 81 with the third room 46.

Moreover, in order to prevent the electrodes 6 and 7 in the first QCM sensor 11a for correction from being corroded by the corrosive gas in the atmosphere, the first room 44 is covered with the shield portion 59b. Furthermore, since there is no need to expose the second QCM sensor 11b that has come to the end of its life to the atmosphere, the second room 45 is also covered with the shield portion 59b.

According to this embodiment described above, the new third QCM sensor 11c for replacement is provided in the sensor unit 80 in advance. Therefore, when the second QCM sensor 11b comes to the end of its life, the user does not need to attach or detach the sensors by user's own hand. Thus, the burden on the user can be reduced.

Moreover, a mechanism to rotate the shutter 59 is very simple. Therefore, one can easily select one of the first to third QCM sensors 11a to 11c that is to be exposed to the atmosphere.

Seventh Embodiment

Although the rotating plate is used as the shutter 59 illustrated in FIG. 33 in the sixth embodiment, a film-like shutter is used in this embodiment.

Figure 38A:
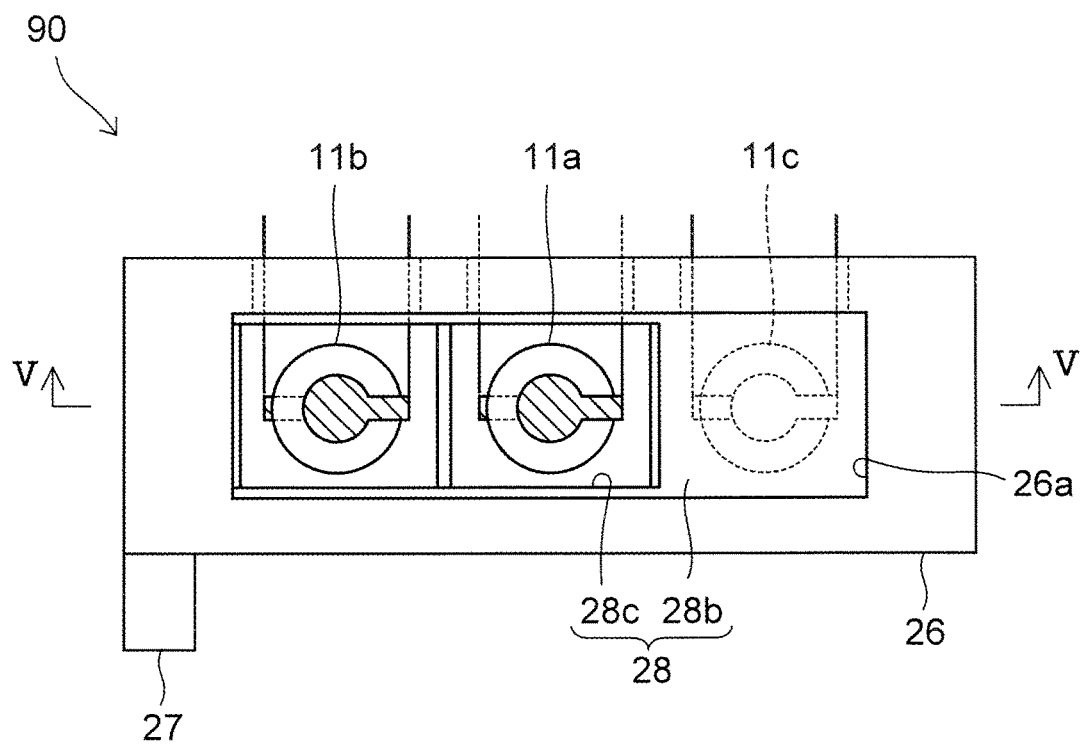
FIG. 38A is a plan view of a sensor unit used in a seventh embodiment.
Figure 38B:
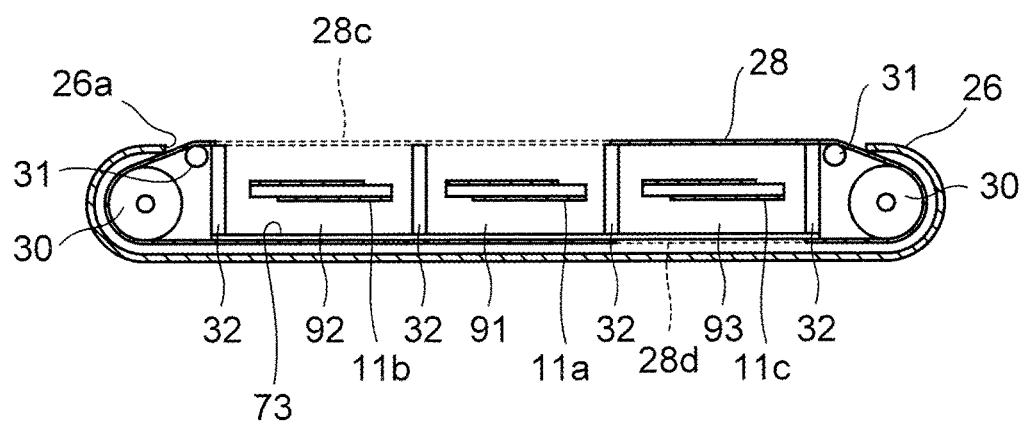
FIG. 38B is a cross-sectional view taken along the line V-V in FIG. 38A.

FIG. 38A is a plan view of a sensor unit 90 used in this embodiment. FIG. 38B is a cross-sectional view taken along the line V-V in FIG. 38A.

Note that, in FIGS. 38A and 38B, the same components as those described with reference to FIGS. 10 to 12 are denoted by the same reference numerals as those in FIGS. 10 to 12, and description thereof is omitted below.

As illustrated in FIG. 38A, in the sensor unit 90, a shutter 28 is moved in a longitudinal direction thereof by rotation of a motor 27.

A first window 28c is provided in the shutter 28. By controlling the amount of movement of the shutter 28, the first to third QCM sensors 11a to 11c can be exposed from the first window 28c or an opening 26a in a housing 26 can be covered with a shield portion 28b of the shutter 28.

Also, as illustrated in FIG. 38B, four partition plates 32 described in the first embodiment are provided in the housing 26, and first to third rooms 91 to 93 are defined by the partition plates 32.

Note that, in this embodiment, ends of the partition plates 32 are connected by a bottom plate 73, and the bottom plate 73 defines bottoms of the first to third rooms 91 to 93.

Figure 39:
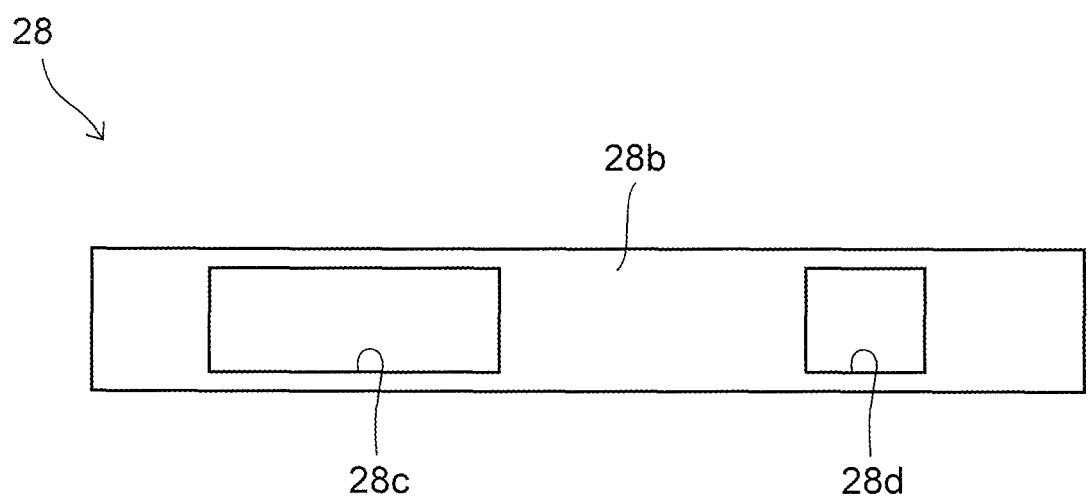
FIG. 39 is a development diagram of a shutter included in the sensor unit used in the seventh embodiment.

FIG. 39 is a development diagram of the shutter 28.

In the shutter 28, the first window 28c and a second window 28d are formed with a space therebetween. The first window 28c is used to expose one or two QCM sensors selected from the first to third QCM sensors 11a to 11c. Meanwhile, the second window 28d is used to expose only the first QCM sensor 11a used for correction.

Figure 40:
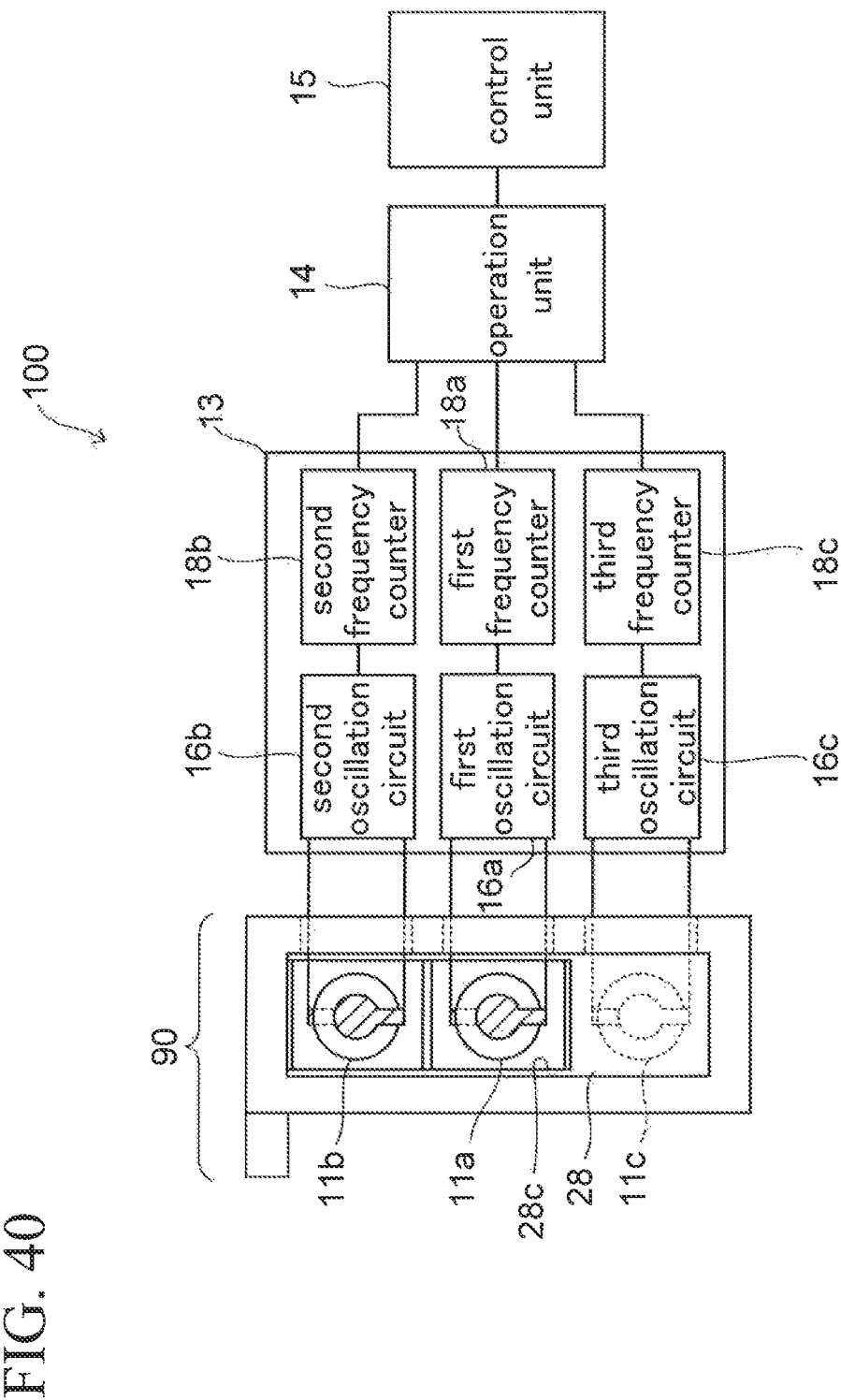
FIG. 40 is a configuration diagram of an environmental measurement apparatus according to the seventh embodiment.

FIG. 40 is a configuration diagram of an environmental measurement apparatus 100 including the sensor unit 90. Note that, in FIG. 40, the same components as those described with reference to FIG. 36 in the sixth embodiment are denoted by the same reference numerals as those in FIG. 36, and description thereof is omitted below.

As illustrated in FIG. 40, the first to third QCM sensors 11a to 11c in the sensor unit 90 are connected to a control unit 15 through a drive unit 13 and an operation unit 14. In this embodiment, the control unit 15 adjusts a movement amount of the shutter 28 by controlling a rotation amount of the motor 27.

Next, operations of the sensor unit 100 are described.

FIGS. 41A to 41E are plan views for explaining the operations of the sensor unit 100.

FIG. 41A illustrates a state where the time t is before a first time $t_s$. At this time, as described with reference to FIG. 28, the second QCM sensor 11b is not close to the end of its life yet, and the amount of corrosion caused by a corrosive gas is measured by using only the second QCM sensor 11b.

Thus, at this time, the second QCM sensor 11b is exposed to the atmosphere containing the corrosive gas by communicating the first window 28c in the shutter 28 with only the second room 92. Moreover, in order to prevent the corrosion of electrodes 6 and 7 in the first QCM sensor 11a for correction and a new third QCM sensor 11c, the first and third rooms 91 and 93 are covered with the shield portion 28b of the shutter 28.

FIG. 41B illustrates a state where the time t is between the first time $t_s$ and a second time $t_c$.

Since this time is within a first period $T_1$ in FIG. 28, correction is performed using both of the first and second QCM sensors 11a and 11b.

Thus, at this time, the first and second QCM sensors 11a and 11b are exposed from the first window 28c by communicating the first window 28c with both of the first and second rooms 91 and 92.

Note that the third room 93 is covered with the shield portion 28b to prevent the corrosion of the electrodes 6 and 7 in the new third QCM sensor 11c.

FIG. 41C illustrates a state where the time t is between the second time $t_c$ and a third time $t_d$.

At this time, as illustrated in FIG. 28, measurement is performed using only the first QCM sensor 11a for correction. Therefore, the first QCM sensor 11a is exposed from the second window 28d by communicating only the second window 28d, which is formed to have a size to expose only one sensor, with the first room 91.

FIG. 41D illustrates a state where the time t is between the third time $t_d$ and a fourth time $t_e$.

Since this time is within a second period $T_2$ described with reference to FIG. 28, correction is performed using both of the first and third QCM sensors 11a and 11c.

Therefore, at this time, the first and third QCM sensors 11a and 11c are exposed from the first window 28c by communicating the first window 28c with both of the first and third rooms 91 and 93.

FIG. 41E illustrates a state where the time t is after the fourth time $t_e$.

At this time, as illustrated in FIG. 28, the amount of corrosion caused by the corrosive gas is measured by using only the third QCM sensor 11c. Therefore, in this case, the third QCM sensor 11c is exposed from the first window 28c by communicating the first window 28c with the third room 93.

Moreover, in order to prevent the electrodes 6 and 7 in the first QCM sensor 11a for correction from being corroded by the corrosive gas in the atmosphere, the first room 91 is covered with the shield portion 28b. Furthermore, since there is no need to expose the second QCM sensor 11b that comes to the end of its life to the atmosphere, the second room 92 is also covered with the shield portion 28b.

According to this embodiment described above, which one of the first to third QCM sensors 11a to 11c is to be exposed to the atmosphere is automatically selected according to the time t, as illustrated in FIGS. 41A to 41E. Thus, the burden on the user can be reduced.

Furthermore, the first to third QCM sensors 11a to 11c are housed in a housing 26 in advance. Therefore, labor for replacing the sensors can be reduced, and hence the labor on the user can be further lessened.

Eighth Embodiment

In the fifth embodiment, as illustrated in FIG. 28, the first period $T_1$ is provided when the life of the second QCM sensor 11b is about to end, and the second change $\Delta f_{2m}$ is corrected using the first change $\Delta f_{1m}$ in the first period $T_1$.

Meanwhile, in this embodiment, a second change $\Delta f_{2m}$ is corrected using a first change $\Delta f_{1m}$ immediately after measurement with a second QCM sensor 11b is started.

Figure 42:
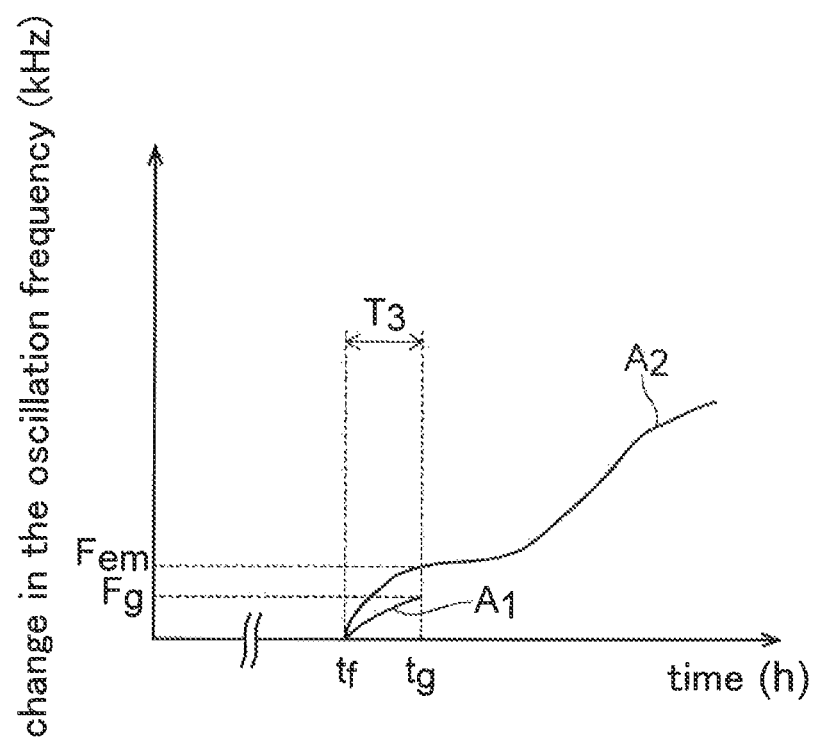
FIG. 42 is a graph illustrating an example of a result of measurement using QCM sensors used in an eighth embodiment.

FIG. 42 is a diagram illustrating an example of measurement results of a first and the second QCM sensors 11a and 11b (see FIG. 24). In FIG. 42, first and second graphs $A_1$ and $A_2$ correspond to the measurement results of the first and second QCM sensors 11a and 11b, respectively.

Note that the horizontal axis of each of the graphs represents time that has elapsed since an arbitrary time. Also, the vertical axis of each graph represents first and second changes $\Delta f_{1m}$ and $\Delta f_{2m}$, which are changes in an oscillation frequency of each of the first and second QCM sensors 11a and 11b.

As illustrated in FIG. 42, in this embodiment, a third period $T_3$ is provided. The third period $T_3$ is provided at the early stage of the measurement using the second QCM sensor 11b, namely, at the beginning of a series of continuous measurements. In the third period $T_3$, measurement is performed using both of the second QCM sensor 11b and the first QCM sensor 11a for correction.

A fifth time $t_f$ which is the beginning of the third period $T_3$, is the time to start acquiring the second oscillation frequency $f_{2m}$ of the second QCM sensor 11b. Also, the fifth time $t_f$ is the time for the operation unit 14 (see FIG. 24) to start calculating the second change $\Delta f_{2m}$ in the second oscillation frequency $f_{2m}$. This time is equal to the time to start acquiring the first oscillation frequency $f_{1m}$ of the first QCM sensor 11a and for the operation unit 14 to start calculating the first change $\Delta f_{1m}$ in the first oscillation frequency $f_{1m}$.

Moreover, a sixth time $t_g$, which is the end of the third period $T_3$, is the time when the second change $\Delta f_{2m}$ reaches a predetermined specified value $F_{em}$. Also, the sixth time $t_g$ is the time when the operation unit 14 finishes acquiring the first oscillation frequency $f_{1m}$ and thus finishes calculating the first change $\Delta f_{1m}$.

As described in the fifth embodiment, even though the first and second QCM sensors 11a and 11b have the same specifications, the individual differences thereof causes a difference in slope between the first and second graphs $A_1$ and $A_2$ during the third period $T_3$.

To deal with this problem, in this embodiment, the following correction is performed to match the slope of the second graph $A_2$ with the slope of the first graph $A_1$.

First, the operation unit 14 calculates a third ratio $F_g/F_{em}$ of the first increment $F_g$ of the first change $\Delta f_{1m}$ within the third period $T_3$ to the second increment $F_{em}$ of the second change $\Delta f_{2m}$ within the third period $1_3$, and sets the third ratio as a third correction coefficient $C_3$. The third correction coefficient $C_3$ thus calculated is equal to a ratio between the slopes of the graphs $A_1$ and $A_2$ in FIG. 42 during the third period $T_3$.

After that, the operation unit 14 corrects the second change $\Delta f_{2m}$ by multiplying the second change $\Delta f_{2m}$ at and after the sixth time $t_g$ by the third correction coefficient $C_3$.

As already mentioned, the third correction coefficient $C_3$ is equal to the ratio between the slopes of the graphs $A_1$ and $A_2$. Therefore, by correcting the second change $\Delta f_{2m}$ in this manner, the slope of the second graph $A_2$ can be matched with the slope of the first graph $A_1$.

All examples and conditional language recited herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An environmental measurement apparatus comprising:
an operation unit which calculates a first change in a first oscillation frequency of a second QCM sensor,
wherein the operation unit corrects the second change based on the first change in a first period and the second change in the first period, and
wherein the operation unit obtains a first ratio of a first increment of the first change within the first period to a second increment of the second change within the first period, and corrects the second change by multiplying the second change by the first ratio.

2. The environmental measurement apparatus according to claim 1, wherein the operation unit starts acquiring the second oscillation frequency at a first time within the first period, and finishes acquiring the first oscillation frequency at a second time within the first period.

3. The environmental measurement apparatus according to claim 2, wherein
the first QCM sensor includes:
a crystal oscillator, a first electrode formed on one main surface of the crystal oscillator, a second electrode formed on the other main surface of the crystal oscillator, where a voltage is to be applied between the second electrode and the first electrode, and a wire formed on at least one of the one main surface and the other main surface, and the operation unit sets as the first time a time when a resistance value of the wire exceeds a predetermined threshold.

4. The environmental measurement apparatus according to claim 2, wherein the operation unit corrects the second change by adding the first change at the first time to a value obtained by multiplying the second change by the first ratio.

5. An environmental measurement method, the method comprising:

calculating a first change in a first oscillation frequency of a first QCM sensor;

calculating a second change in a second oscillation frequency of a second QCM sensor;

correcting the second change based on the first change in a first period and the second change in the first period; and obtaining a first ratio of a first increment of the first change within the first period to a second increment of the second change within the first period, wherein the correcting the second change includes correcting the second change by multiplying the second change by the first ratio.

* * * * *